(12) United States Patent
Yi et al.

(10) Patent No.: US 11,850,297 B2
(45) Date of Patent: Dec. 26, 2023

(54) COMPOSITION COMPRISING SAPOGENIN AND EXOSOME AS EFFECTIVE INGREDIENT

(71) Applicant: ExoCoBio Inc., Seoul (KR)

(72) Inventors: Yong Weon Yi, Seoul (KR); Byong Seung Cho, Gunpo-si (KR)

(73) Assignee: ExoCoBio Inc., Seoul (KR)

( * ) Notice: Subject to any disclaimer, the term of this patent is extended or adjusted under 35 U.S.C. 154(b) by 952 days.

(21) Appl. No.: 16/823,582

(22) Filed: Mar. 19, 2020

(65) Prior Publication Data

US 2020/0222298 A1 Jul. 16, 2020

Related U.S. Application Data

(63) Continuation of application No. PCT/KR2018/011316, filed on Sep. 21, 2018.

(30) Foreign Application Priority Data

Sep. 30, 2017 (KR) .................. 10-2017-0128463
Sep. 13, 2018 (KR) .................. 10-2018-0109879

(51) Int. Cl.
*A61K 8/63* (2006.01)
*A61Q 19/00* (2006.01)
*A61K 8/96* (2006.01)

(52) U.S. Cl.
CPC ............ *A61K 8/63* (2013.01); *A61K 8/96* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 2003/0216327 A1 | 11/2003 | Rubinstenn et al. | |
| 2012/0315324 A1 | 12/2012 | Zhang | |

FOREIGN PATENT DOCUMENTS

| | | |
|---|---|---|
| CN | 107106613 A | 8/2017 |
| EP | 1 375 509 A1 | 1/2004 |
| EP | 3 189 828 A1 | 7/2017 |
| JP | 2009-545582 A | 12/2009 |
| KR | 10-2004-0098878 A | 11/2004 |
| KR | 10-2016-0076654 A | 7/2016 |
| KR | 10-2016-0110410 A | 9/2016 |
| WO | 2008/015639 A2 | 2/2008 |
| WO | 2015/110957 A2 | 7/2015 |
| WO | WO-2016072821 A1 * | 5/2016 ............ A61K 35/12 |

OTHER PUBLICATIONS

Jesus et al. (Diosgenin: Recent Highlights on Pharmacology and Analytical Methodology, Journal of Analytical Methods in Chemistry, vol. 2016, 1-16). (Year: 2016).*
Honli Zhang et al., "Deratization Plants in China Research Methods", Northwest A&F University Press, Nov. 30, 2009, pp. 334 (5 pages total).
"Academic Yearbook of Chinese Traditional Medicine", National Administration of Traditional Chinese Medicine, Shanghai University Press of Traditional Chinese Medicine, Dec. 31, 2004, pp. 56 (5 pages total).
Office Action dated Jul. 19, 2022 issued by the Chinese Patent Office in Chinese Application No. 201880062704.8.
Xiaobing Fu, "Regenerative Medicine—From Basic to Clinical Research", Shanghai Scientific & Technical Publishers, Mar. 31, 2008 (4 pages total).
Yuanxun Yu et al., "Chinese Molecular Diabetology", Anhui Science and Technology Publishing House, Apr. 30, 2016 (5 pages total).
Din Ha, et al., "Exosomes as therapeutic drug carriers and delivery vehicles across biological membranes: current perspectives and future challenges", Acta Pharmaceutica Sinica B, 2016, pp. 287-296, vol. 6, No. 4.
International Search Report for PCT/KR2018/011316 dated Jan. 7, 2019 (PCT/ISA/210).

* cited by examiner

Primary Examiner — Aaron J Kosar
Assistant Examiner — Jacob A Boeckelman
(74) Attorney, Agent, or Firm — Sughrue Mion, PLLC

(57) ABSTRACT

A composition containing a combination of exosomes and sapogenin as an active ingredient is disclosed. The composition is able to promote preadipocyte proliferation, lipid uptake into adipocytes, and/or adipogenesis, but reduce the cytotoxicity caused by sapogenin. Therefore, the composition can reduce side effects on the body or skin, and can be used such that it is conveniently applied to a dissatisfactory part of the body showing flaws which look less plump due to a deficit in lipids and the like, or an area of the skin showing flaws caused by a deficit in lipids.

6 Claims, 30 Drawing Sheets
(2 of 30 Drawing Sheet(s) Filed in Color)
Specification includes a Sequence Listing.

Control

Diosgenin + Exosome

Scale bar: 50 μm

Control | Pioglitazone
Diosgenin | Diosgenin + Exosome

Scale bar: 50 μm

Control

Diosgenin

Diosgenin + Exosome

Scale bar: 50 μm

COMPOSITION COMPRISING SAPOGENIN AND EXOSOME AS EFFECTIVE INGREDIENT

CROSS REFERENCE

This application is a Bypass Continuation of International Application No. PCT/KR2018/011316 filed Sep. 21, 2018, claiming priority based on Korean Patent Application No. 10-2017-0128463 filed Sep. 30, 2017 and Korean Patent Application No. 10-2018-0109879 filed Sep. 13, 2018, the entire contents of which are incorporated herein by reference.

TECHNICAL FIELD

The present invention relates to a composition comprising the combination of sapogenin and exosomes as an active ingredient, and more particularly to a composition for the prevention, alleviation, amelioration or recovery of a part of the body showing flaws which look less plump due to a deficit in lipids and the like, or an area of the skin showing flaws caused by a deficit in lipids.

Moreover, the present invention relates to a cosmetic composition and a skin external preparation including the above composition.

BACKGROUND ART

As an interest in the looks of the face or body, etc. increases, the demand for cosmetics is also increasing to improve skin conditions and to embellish inferior parts of the looks. In particular, there is a growing interest in cosmetic procedures aimed at ameliorating skin wrinkles and another conditions of skin appearance. For example, there is a method of ameliorating skin wrinkles by topically injecting Botulinum toxin or a filler into the skin.

In recent years, much attention has been paid to cosmetic procedures that can volumize a part of the body showing flaws which look less plump due to a deficit in lipids and the like (so-called "a part of the body suffering from inferiority complex") and make the part of the body look beautiful. Since a filler has a volumizing effect, it can be topically applied to parts of the body showing flaws, for example, lips, nose, forehead, cheeks, breasts, genitals and the like, which look less plump, and volumize the parts of the body. However, a hyaluronic acid filler has a problem that the filler is degraded in the body over time, and thus needs to be injected periodically into a part of the body showing flaws in order to keep the part of the body volumized. In addition, the filler injection has a problem that it is painful.

Therefore, it is necessary to develop a new cosmetic material that can introduce fat into a dissatisfactory part of the body showing flaws which look less plump due to a deficit in lipids and the like, or an area of the skin showing flaws caused by a deficit in lipids to volumize the parts of the body or the area of the skin, but does not cause pain and is easy to use. In this connection, a method for expanding subcutaneous fat tissue using a plant extract containing sarsasapogenin has been proposed. However, sarsasapogenin should be improved in terms of the stability of its formulation, the possibility of side effects caused by its cytotoxicity, and the enhancement of its efficacy.

Recently, there have been reports that cell secretomes contain various bioactive molecules that regulate cellular behaviors. In particular, cell secretomes contain 'exosome' that has intercellular signaling functions, and thus studies on the components and functions thereof have been actively conducted.

Cells shed various membraneous vesicles to their extracellular environment, and these released vesicles are usually called extracellular vesicles (EVs). The extracellular vesicle is also called cell membrane-derived vesicle, ectosome, shedding vesicle, microparticle, exosome, etc., and is also used discriminately from exosome in some cases.

Exosome is a vesicle of tens to hundreds of nanometers in size, which consists of a phospholipid bilayer membrane having the same structure as that of the cell membrane. This exosome contains proteins, nucleic acids (mRNA, miRNA, etc.) and the like which are called exosome cargo. It is known that exosome's cargo includes a wide range of signaling factors, and these signaling factors are specific for cell types and regulated differently depending on secretory cells' environment. It is known that exosome is an intercellular signaling mediator secreted by cells, and various cellular signals transmitted through it regulate cellular behaviors, including the activation, growth, migration, differentiation, dedifferentiation, apoptosis, and necrosis of target cells. Exosome contains specific genetic materials and bioactive factors depending on the nature and state of cells from which the exosome was derived. Exosome derived from proliferating stem cells regulates cell behaviors such as cell migration, proliferation and differentiation, and recapitulates the characteristics of stem cells involved in tissue regeneration (Nature Review Immunology 2002 (2) 569-579).

However, although various studies of exosomes have been conducted, which suggest the possibility for the treatment of some diseases using exosomes, not much attention has been paid to the development of new formulations which can stably maintain and make exosomes stored, and the linking of exosomes with various medical or cosmetic technologies for increasing the convenience and efficacy of exosomes.

The present inventors have conducted extensive studies on new applications of exosomes and the linking of exosomes with medical or cosmetic technology, and as a result, have found that the combination of sapogenin and exosomes promotes preadipocyte proliferation, lipid uptake into adipocytes and adipogenesis, but reduces the cytotoxicity caused by sapogenin, thereby completing the present invention.

Meanwhile, it is to be understood that the matters described as the background art are intended merely to aid in the understanding of the background of the present invention and are not admitted as prior art against the present invention.

SUMMARY OF INVENTION

An object of the present invention is to provide a composition comprising the combination of sapogenin and exosomes as an active ingredient for the prevention, alleviation, amelioration or recovery of a part of the body showing flaws which look less plump due to a deficit in lipids and the like, or an area of the skin showing flaws caused by a deficit in lipids.

Another object of the present invention is to provide a functional cosmetic composition and a skin external preparation including the above composition.

Still another object of the present invention is to provide a cosmetic method except for treatment purposes, which comprises topically applying the above composition to a part of the body showing flaws or an area of the skin showing flaws of a mammal, and volumizing the part of the body or the area of the skin having the composition applied thereto.

However, the objects of the present invention as described above are illustrative and the scope of the present invention is not limited thereby. In addition, other objects and advantages of the present invention will be more apparent from the following description, the appended claims and the accompanying drawings.

DETAILED DESCRIPTION OF INVENTION

To achieve the above objects, the present invention provides a composition comprising the combination of sapogenin and exosomes as an active ingredient for preventing, alleviating, ameliorating or recovering a part of the body showing flaws or an area of the skin showing flaws caused by a deficit in lipids.

As used herein, the term "exosomes" refers to vesicles of tens to hundreds of nanometers in size (preferably, about 30 to 200 nm), which consist of a phospholipid bilayer membrane having the same structure as that of the cell membrane (however, the particle size of exosomes is variable depending on the type of cell from which the exosomes are isolated, an isolation method and a measurement method) (Vasiliy S. Chernyshev et al., "Size and shape characterization of hydrated and desiccated exosomes", Anal Bioanal Chem, (2015) DOI 10.1007/s00216-015-8535-3). These exosomes contain proteins, nucleic acids (mRNA, miRNA, etc.) and the like which are called exosome cargo. It is known that exosomes' cargo includes a wide range of signaling factors, and these signaling factors are specific for cell types and regulated differently depending on secretory cells' environment. It is known that exosomes are intercellular signaling mediators secreted by cells, and various cellular signals transmitted through them regulate cellular behaviors, including the activation, growth, migration, differentiation, dedifferentiation, apoptosis, and necrosis of target cells.

As used herein, the term "sapogenin" refers to aglycones of saponins, some of which are distributed as a free form in the plant system. Sapogenin is a naturally derived compound extractable from various plants, and is known to improve the blood flow and have antitussive, expectorant, diuretic and anticancer effects. The type of sapogenin is not limited, but as an example, not limiting the present invention, the sapogenin may be diosgenin, hecogenin, smilagenin, epismilagenin, sarsasapogenin, isosarsasapogenin, episarsasapogenin, parigenin, tigogenin, epitigogenin, neotigogenin, parillin, timosaponin, xilingsaponin, filiferin, yamogenin, or yuccagenin, and preferably, it may be diosgenin.

As used herein, the term "biological solution" refers to a liquid solution having biological origin in which exosomes are dispersed, suspended, precipitated, floated or mixed. Examples of the biological solution include conditioned media of cell cultures, supernatants of cell cultures, conditioned media of stem cell cultures, supernatants of stem cell cultures, whole blood, serum, umbilical cord blood, plasma, ascitic fluids, brain and cerebrospinal fluids, placental extracts, and bone marrow aspirates. However, it is to be understood that the present invention is not limited thereto and does not exclude solutions originating from various organisms, such as various animals, plants, bacteria, fungi, algae, and the like. The biological solution may be cultured or incubated under conditions that release and/or secrete exosomes, and may also be frozen and thawed.

Meanwhile, the term "exosomes" as used herein is intended to include all vesicles (e.g., exosome-like vesicles) which are secreted from the cells (preferably, stem cells) of various animals, plants, bacteria, fungi, algae or the like and released into extracellular spaces, and have a nano-sized vesicle structure and a composition similar to that of exosomes.

However, as exosomes used in the present invention, various exosomes that are being used in the art or may be used in the future may, of course, be used as long as they are effective in preventing, alleviating, ameliorating or recovering a part of the body showing flaws which look less plump due to a deficit in lipids and the like, or an area of the skin showing flaws caused by a deficit in lipids, and do not cause adverse effects on the human body. Therefore, it should be noted that exosomes isolated according to the isolation method of Examples described below should be understood as an example of exosomes that may be used in the present invention, and the present invention is not limited thereto.

As used herein, the term "a part of the body showing flaws" or "an area of the skin showing flaws" refers to body parts which look less plump due to a deficit in lipids and the like, for example, small breasts or genitals, or skin areas lacking subcutaneous fat, and the like. The part of the body showing flaws or the area of the skin showing flaws may result in, for example, sagging skin, sunken cheeks, hollow eyes, skin wrinkles (e.g., facial wrinkles, neck wrinkles, hand wrinkles, etc.), decreased skin elasticity, fine lines, wrinkles, rough and deep wrinkles, skin cracks, bumps, dry skin, and the like.

In addition, the term "volumizing" as used herein may refer to 1) "volumizing a dissatisfactory part of the body which looks less plump due to a deficit in lipids and the like", 2) "preventing, alleviating, ameliorating or recovering an area of the skin showing flaws caused by a deficit in lipids", or 3) "making the body or skin look beautiful" by the above 1) and/or 2). As an example, not limiting the present invention, the expression "preventing, alleviating, ameliorating or recovering a part of the body showing flaws which look less plump due to a deficit in lipids and like, or an area of the skin showing flaws caused by a deficit in lipids" includes processes of promoting preadipocyte proliferation, lipid uptake into adipocytes, and/or adipogenesis, and stimulating the introduction and growth of adipocytes into the area of the skin showing a deficit in lipids. This introduction and growth of adipocytes can remarkably increase the thickness of the skin step by step, resulting in plumpness, volume-up and skin tightening effects, making the skin elastic, and preventing, alleviating, ameliorating or removing the skin flaws.

For example, the expression "preventing, alleviating, ameliorating or recovering a part of the body showing flaws which look less plump due to a deficit in lipids and like, or an area of the skin showing flaws caused by a deficit in lipids" may include preventing, alleviating, ameliorating or removing sagging skin, sunken cheeks, hollow eyes, skin wrinkles (e.g., facial wrinkles, neck wrinkles, hand wrinkles, etc.), decreased skin elasticity, fine lines, wrinkles, rough and deep wrinkles, skin cracks, bumps, scars, stretch marks, etc., or restoring those conditions to normal states; skin regeneration, adipose tissue regeneration, contour correction, correction of flaws of soft tissue, tissue enlargement, volume-up, breast enlargement, genital enlargement, skin moisturization, and the like. However, the expression "preventing, alleviating, ameliorating or recovering a part of the body showing flaws which look less plump due to a deficit in lipids and the like, or an area of the skin showing flaws caused by a deficit in lipids" in the present invention is not limited to those described above, and may include promoting preadipocyte proliferation, lipid uptake into adipocytes, and/or adipogenesis, and stimulating the introduction and growth of adipocytes into an area showing a deficit in lipids, thereby preventing, alleviating, ameliorating, removing or recovering a part of the body showing flaws or an area of the skin showing flaws which represent a deficit in lipids due to various causes.

The composition according to one embodiment of the present invention comprises the combination of exosomes and sapogenin as an active ingredient.

In the composition according to one embodiment of the present invention, the combination of exosomes and sapogenin may be obtained by incubating exosomes with sapogenin.

In the composition according to one embodiment of the present invention, the combination of exosomes and sapogenin may be obtained by mixing the exosomes with the sapogenin, and incubating the mixture of the exosomes and the sapogenin. In the combination of exosomes and sapogenin, the sapogenin may be penetrated into the exosomes or at least associated with the exosomes to be loaded in the exosomes.

The composition according to one embodiment of the present invention may promote at least one of preadipocyte proliferation, lipid uptake into adipocytes, or adipogenesis. Additionally, the composition according to one embodiment of the present invention may reduce the cytotoxicity caused by the sapogenin.

As an example, not limiting the present invention, the exosomes may be obtained by performing the following steps: (a) adding trehalose to a biological solution; (b) filtering the biological solution having the trehalose added thereto; (c) isolating exosomes from the filtered biological solution by tangential flow filtration (TFF); and (d) adding trehalose to a buffer for diafiltration, and performing diafiltration on the isolated exosomes by TFF using the buffer having the trehalose added thereto.

Meanwhile, when trehalose is added to the buffer for diafiltration in step (d), exosomes having a uniform particle size distribution and high purity can be effectively obtained (see FIGS. 6A to 6E). In the present invention, exosomes having a uniform particle size distribution and high purity can be obtained in high yield by using trehalose in the prefiltration process (step (b)) prior to the exosome isolation using the TFF and the diafiltration process (step (d)) using the TFF after the exosome isolation. Meanwhile, in the present invention, trehalose serves to efficiently discriminate exosomes from impurities such as cell debris, waste, proteins and macroparticles.

The diafiltration may be performed continuously or discontinuously. The diafiltration may be performed using a buffer having at least 4 times, preferably at least 6 to 10 times, more preferably at least 12 times volume of the isolated exosomes. In addition, TFF may be performed using either a TFF filter having a molecular weight cutoff (MWCO) of 100,000 Da (Dalton), 300,000 Da, 500,000 Da or 750,000 Da, or a 0.05 μm filter. The step (c) may further comprise concentrating the isolated exosomes to a volume of 1/100 to 1/25 by the TFF.

As an example, not limiting the present invention, the biological solution may be a conditioned medium of stem cell cultures. The stem cells are not limited to the kind thereof, but may preferably be mesenchymal stem cells, for example, adipose-, bone marrow-, umbilical cord- or umbilical cord blood-derived stem cells, more preferably adipose-derived stem cells. The adipose-derived stem cells are not limited to the kind thereof as long as they have no risk of infection with pathogens and do not cause immune rejection, but may preferably be human adipose-derived stem cells.

However, the exosomes used in the present invention are not limited to the exosomes obtained by the above-described isolation method, and it is of course possible to use various exosomes that are being used in the art or may be used in the future. It should be noted that the exosomes isolated according to the isolation method should be understood as an example of exosomes that may be used in the composition of the present invention, and the present invention is not limited thereto.

The composition according to one embodiment of the present invention may be effectively used to prevent, alleviate, ameliorate or recover a part of the body showing flaws which look less plump due to a deficit in lipids and the like, or an area of the skin showing flaws caused by a deficit in lipids.

The composition according to one embodiment of the present invention may be a functional cosmetic composition or a skin external preparation.

Meanwhile, when the composition according to one embodiment of the present invention is prepared as a skin external preparation and/or a cosmetic composition, it may suitably contain components which are generally used in cosmetic products or skin external preparations, for example, moisturizers, antioxidants, oily components, UV absorbers, emulsifiers, surfactants, thickeners, alcohols, powder components, colorants, aqueous components, water, and various skin nutrients, etc., as needed, within the range that does not impair the effect of the present invention.

Furthermore, the skin external preparation and/or cosmetic composition according to one embodiment of the present invention may include, in addition to the combination of sapogenin and exosomes, components exhibiting tissue enlargement or reconstruction characteristics, which have been used in the prior art, as long as these components do not impair the effect of the combination (i.e., the effect of preventing, alleviating, ameliorating or recovering a part of the body showing flaws which look less plump due to a deficit in lipids and the like, or an area of the skin showing flaws caused by a deficit in lipids). For example, sapogenin and exosomes constituting of the composition of the present invention may be contained in or mixed with at least one of hydrogel, hyaluronic acid, salt of hyaluronic acid (e.g., sodium hyaluronate, etc.), or hyaluronate gel. In the skin external preparation and/or cosmetic composition according to one embodiment of the present invention, the kind of hydrogel is not particularly limited, but the hydrogel may be preferably obtained by dispersing a gelled polymer in a polyhydric alcohol. The gelled polymer may be at least one selected from the group consisting of pluronic, purified agar, agarose, gellan gum, alginic acid, carrageenan, cassia gum, xanthan gum, galactomannan, glucomannan, pectin, cellulose, guar gum, and locust bean gum, and the polyhydric alcohol may be at least one selected from the group consisting of ethylene glycol, propylene glycol, 1,3-butylene glycol, isobutylene glycol, dipropylene glycol, sorbitol, xylitol, and glycerin.

The skin external preparation and/or cosmetic composition according to one embodiment of the present invention may be used in various forms, for example, patches, mask packs, mask sheets, creams, tonics, ointments, suspensions, emulsions, pastes, lotions, gels, oils, packs, sprays, aerosols, mists, foundations, powders, and oilpapers. For example, the skin external preparation and/or cosmetic composition may be applied to or soaked in at least one surface of a patch, a mask pack or a mask sheet.

When the composition according to one embodiment of the present invention is prepared as a cosmetic composition, it is used for the purpose of preventing, ameliorating, alleviating or recovering a dissatisfactory part of the body showing flaws which are less plump due to a deficit in lipids and the like, or an area of the skin showing flaws caused by a deficit in lipids, and the cosmetic composition may be prepared as any formulation which is generally prepared in the art. For example, it may be formulated as patch, mask pack, mask sheet, skin softener, nutrition, astringent lotion, nourishing cream, massage cream, eye cream, cleansing cream, essence, eye essence, cleansing lotion, cleansing foam, cleansing water, sunscreen, lipstick, soap, shampoo, surfactant-containing cleanser, bath preparation, body lotion, body cream, body oil, body essence, body cleanser, hairdye, hair tonic, etc., but is not limited thereto.

The skin external preparation and/or cosmetic composition according to one embodiment of the present invention contains components which are commonly used in skin external preparations and/or cosmetic products. For example, the skin external preparation and/or cosmetic composition may contain conventional adjuvants and carriers, such as antioxidants, stabilizers, solubilizers, vitamins, pigments, and fragrances. In addition, other components in each formulation for the skin external preparation and/or cosmetic composition may be suitably selected without difficulty by those skilled in the art depending on the type or intended use of skin external preparation and/or cosmetic composition.

Another embodiment of the present invention provides a cosmetic method except for treatment purposes, which comprises topically applying the above composition to a part of the body showing flaws or an area of the skin showing flaws of a mammal, and volumizing the part of the body or the area of the skin having the composition applied thereto. For example, the volumizing may be skin plumpness, volume-up, skin tightness or skin elasticity improvement.

The cosmetic method according to one embodiment of the present invention includes: (a) applying the composition directly to a mammalian skin; or (b) contacting or attaching a patch, a mask pack or a mask sheet, which has the composition applied thereto or soaked therein, to the mammalian skin; or sequentially performing (a) and (b).

ADVANTAGEOUS EFFECTS

The composition of the present invention, which comprises the combination of sapogenin and exosomes as an active ingredient, is able to promote preadipocyte proliferation, lipid uptake into adipocytes and/or adipogenesis, but reduce the cytotoxicity caused by the sapogenin. Therefore, the composition of the present invention can reduce side effects on the body or skin, and can be used such that it is conveniently applied to a dissatisfactory part of the body showing flaws which look less plump due to a deficit in lipids and the like, or an area of the skin showing flaws caused by a deficit in lipids.

In addition, the composition of the present invention is able to remarkably increase the thickness of the skin step by step, by the introduction and growth of adipocytes, thereby exhibiting correction of skin flaws, plumpness, volume-up and skin tightening effects. Therefore, the composition of the present invention is useful as a functional cosmetic composition and a skin external preparation for promoting lipid uptake into adipocytes and adipogenesis and stimulating the introduction and growth of adipocytes in an area of the skin showing a deficit in lipids.

It should be understood that the scope of the present is not limited to the aforementioned effects.

BRIEF DESCRIPTION OF DRAWINGS

The patent or application file contains at least one drawing executed in color. Copies of this patent or patent application publication with color drawing(s) will be provided by the Office upon request and payment of the necessary fee.

"FIG. 4A" shows the particle size distribution and the number of particles obtained by tunable resistive pulse sensing (TRPS) analysis. "FIG. 4B" shows the particle size distribution and the number of particles obtained by nanoparticle tracking analysis (NTA). "FIG. 4C" shows different magnifications of particle images obtained by transmitted electron microscopy (TEM) analysis. "FIG. 4D" shows the results of Western blot analysis of exosomes obtained according to one embodiment of the present invention. "FIG. 4E" shows the results of flow cytometry for CD63 and CD81 in the analysis of markers for exosomes obtained according to one embodiment of the present invention.

"FIG. 6A" shows the results obtained when trehalose was added throughout the preparation process; "FIG. 6B" shows the results obtained in the case that conditioned media are freeze-stored and thawed, and then trehalose was added to the thawed media; and "FIG. 6C" shows the results obtained when no trehalose was added.

FIG. 11 illustrates that dead cells lost their original shape, and detached from the bottom and floated in the medium.

EXAMPLES

Figure 1:
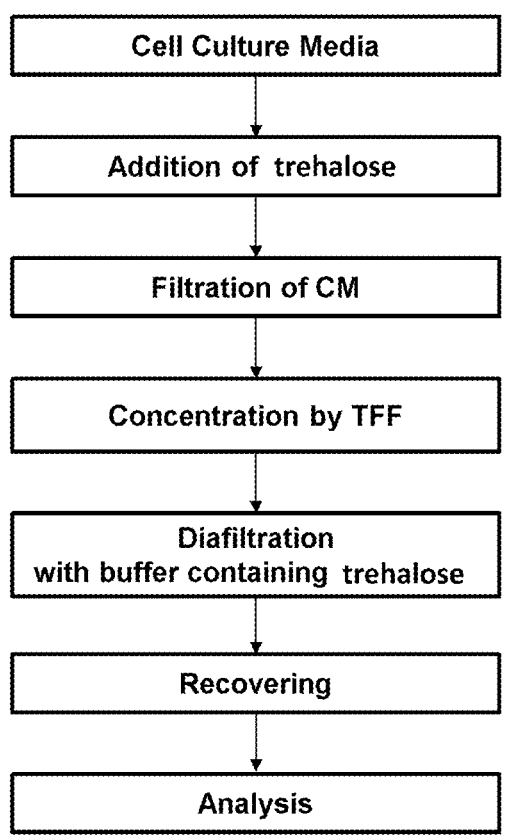
FIG. 1 is a flowchart illustrating a method of isolating and purifying exosomes in a method of preparing exosomes from a biological solution according to one embodiment of the present invention.

Hereinafter, the present invention will be described in more detail with reference to the following examples. However, the following examples are only to illustrate the present invention and are not intended to limit or restrict the scope of the present invention. Those that can be easily inferred by those skilled in the art from the detailed description and examples of the present invention are interpreted as falling within the scope of the present invention. References referred to in the present invention are incorporated herein by reference.

Throughout the present specification, it is to be understood that, when any part is referred to as "comprising" any component, it does not exclude other components, but may further include other components, unless otherwise specified.

Example 1: Cell Culture

Human dermal fibroblast (HDF) HS68 cells purchased from ATCC were subcultured in DMEM (purchased from ThermoFisher Scientific) medium containing 10% fetal bovine serum (FBS; purchased from ThermoFisher Scientific) and 1% antibiotics-antimycotics (purchased from ThermoFisher Scientific) at 37° C. under 5% $CO_2$. Furthermore, 3T3-L1 preadipocytes purchased from ATCC were subcultured in DMEM (purchased from ThermoFisher Scientific) containing 10% NBCS (New Born Calf Serum) and 1% penicillin/streptomycin at 37° C. under 5% $CO_2$.

According to a cell culture method known in the technical field to which the present invention pertains, adipose-derived stem cells were cultured at 37° C. under 5% $CO_2$. Next, the cells were washed with phosphate-buffered saline (purchased from ThermoFisher Scientific), and then the medium was replaced with serum-free, phenol red-free medium, and the cells were cultured for 1 to 10 days. The supernatant (hereinafter, referred to as "conditioned medium (CM)") was recovered.

In order to obtain exosomes having a uniform particle size distribution and high purity in an exosome isolation process, 2 wt % of trehalose was added to the conditioned medium. After addition of trehalose, the conditioned medium was filtered through 0.22 μm filter to remove impurities, such as cell debris, waste, macroparticles and the like. From the filtered conditioned medium, exosomes were immediately isolated. In addition, the filtered conditioned medium was stored in a refrigerator (10° C. or below), and then used for exosome isolation. Furthermore, the filtered conditioned medium was freeze-stored in an ultra-low temperature freezer at −60° C. or below, thawed, and then subjected to exosome isolation. Thereafter, exosomes were isolated from the conditioned medium by TFF.

Example 2: Isolation and Purification of Exosomes by TFF Method

For isolating, concentrating and diafiltrating exosomes from the conditioned medium filtered through 0.22 μm filter in Example 1, TFF method was used. As a filter for TFF method, a cartridge filter (also known as a hollow fiber filter; purchased from GE Healthcare) or a cassette filter (purchased from Pall, Sartorius, or Merck Millipore) was used. The TFF filter may be selected with various molecular weight cutoffs (MWCOs). Using the filter having selected MWCO, exosomes were isolated and concentrated, and particles, proteins, lipids, nucleic acids, low-molecular-weight compounds, etc., were removed, which are smaller than the MWCO.

To isolate and concentrate exosomes, a TFF filter having MWCO of 100,000 Da (Dalton), 300,000 Da or 500,000 Da was used. Exosomes were isolated from the conditioned medium by removing substances smaller than the MWCO and concentrating the conditioned medium to a volume of about 1/100 to 1/25 by the TFF method.

The isolated and concentrated solution of exosomes was additionally subjected to diafiltration using TFF method. The diafiltration was performed continuously (continuous diafiltration) or discontinuously (discontinuous diafiltration), using a buffer having at least 4 times, preferably at least 6 to 10 times, more preferably at least 12 times volume of the isolated exosomes. To obtain exosomes having a uniform particle size distribution and high purity, 2 wt % trehalose in PBS was added to the buffer. FIGS. 6A to 6E show the results that by the addition of trehalose, exosomes having a uniform particle size distribution and high purity can be obtained in high yield.

Example 3: Analysis of Characteristics of Isolated Exosomes

Figure 2:
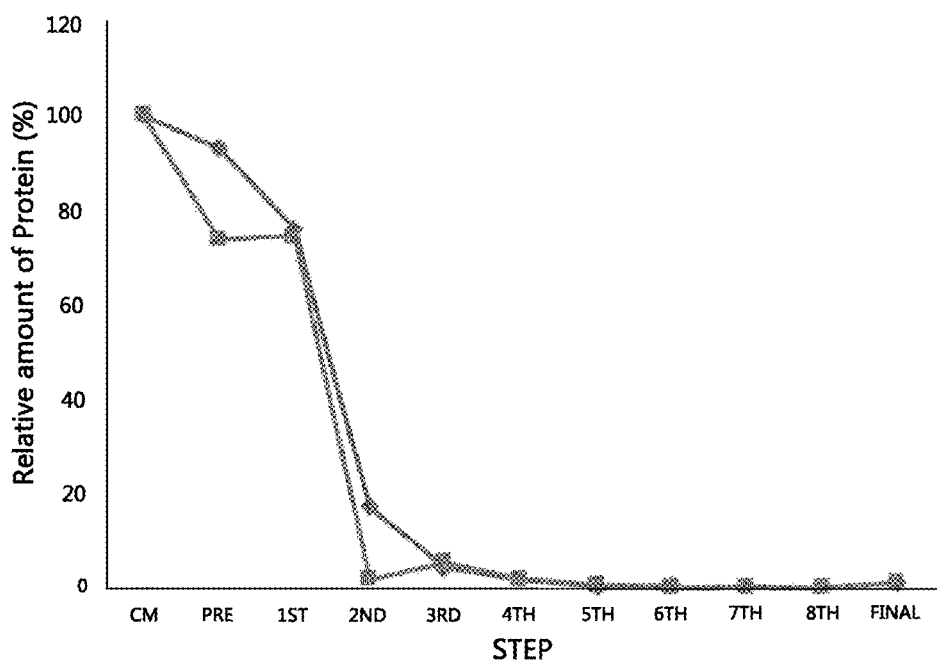
FIG. 2 shows the results of measuring the relative amount of proteins contained in a solution in each step of preparing exosomes from a biological solution, for example culture media of stem cells according to one embodiment of the present invention. The relative amount of proteins in each step was expressed as the relative ratio of the total amount of proteins in solution of each step to the total amount of proteins in the biological solution. The experimental results as shown are the results obtained from two different batches, respectively.

The amounts of proteins of the isolated exosomes, the conditioned medium, and the fractions of TFF isolation process were measured using BCA colorimetric assay (purchased from ThermoFisher Scientific) or FluoroProfile fluorescence assay (purchased from Sigma). With regard to exosomes isolated and concentrated by the TFF method according to one embodiment, the extent, to which proteins, lipids, nucleic acids, low-molecular-weight compounds, etc. were removed, was monitored by the protein assays, and the results of the monitoring are shown in FIG. 2. As a result, it could be seen that proteins present in the conditioned medium were very effectively removed by the TFF method according to one embodiment.

Figure 3:
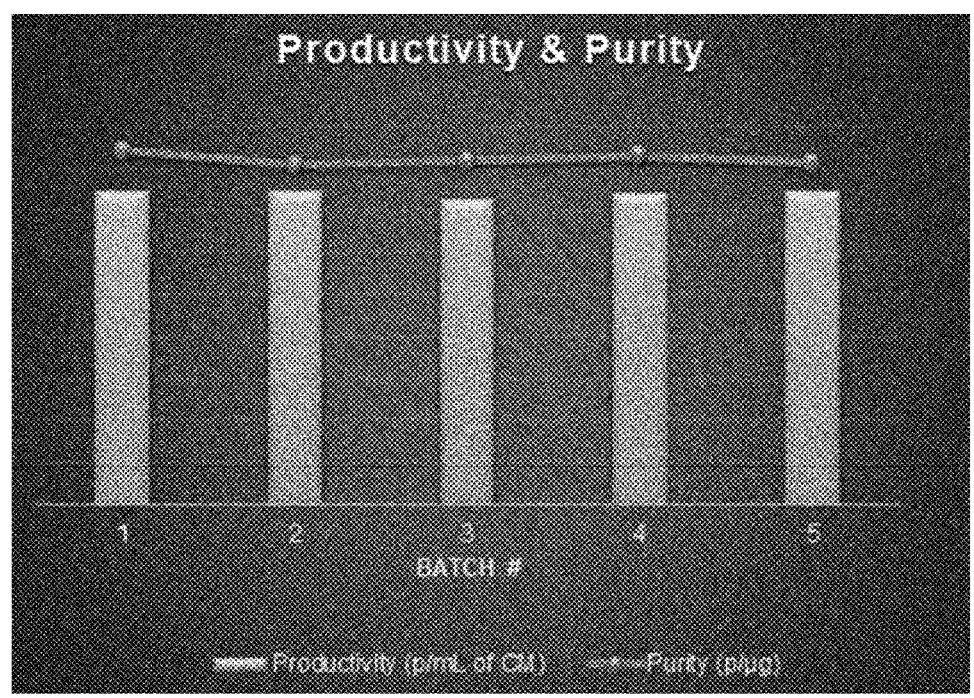
FIG. 3 shows the results of measuring the productivity and purity of exosomes obtained according to one embodiment of the present invention. The productivity of exosomes was calculated as the number of exosome particles obtained per mL of a biological solution, for example conditioned media of stem cells (CM), and the purity of exosomes was calculated as the number of exosome particles per μg of proteins contained in a final fraction. The experimental results as shown are the results obtained from five different batches, respectively.

FIG. 3 shows the results of comparing the productivity and purity of exosomes in each of five independent batches when exosomes were isolated by the TFF method according to one embodiment. The results obtained from the five independent batches were analyzed, and as a result, it was confirmed that exosomes were very stably isolated by the TFF method according to one embodiment.

Figure 4A:
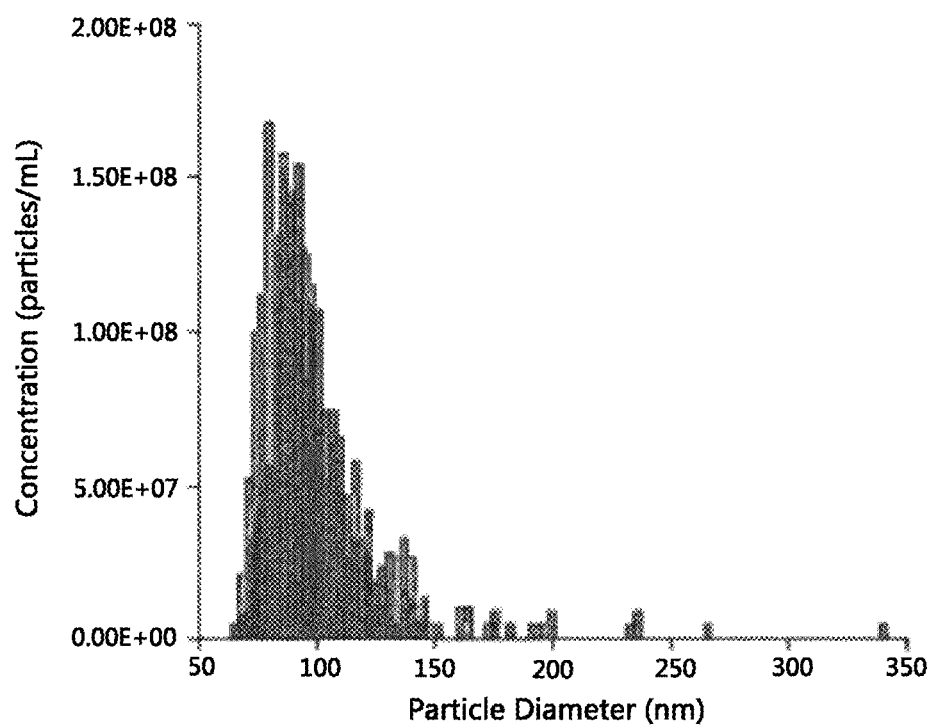
FIGS. 4A to 4E show the results of analyzing the physical properties of exosomes obtained according to one embodiment of the present invention.
Figure 4B:
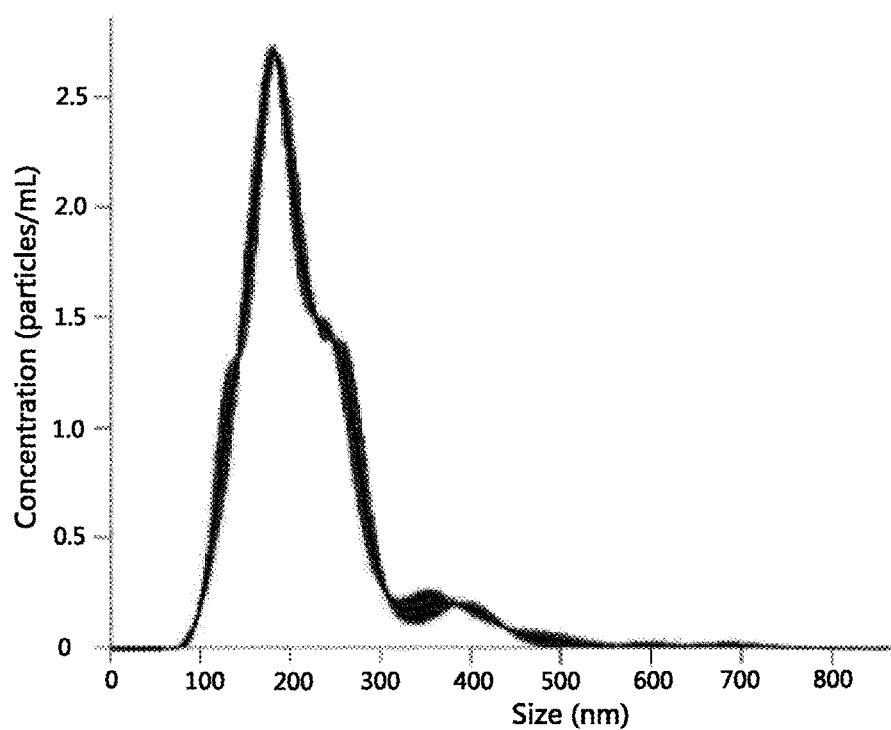
Figure 4C:
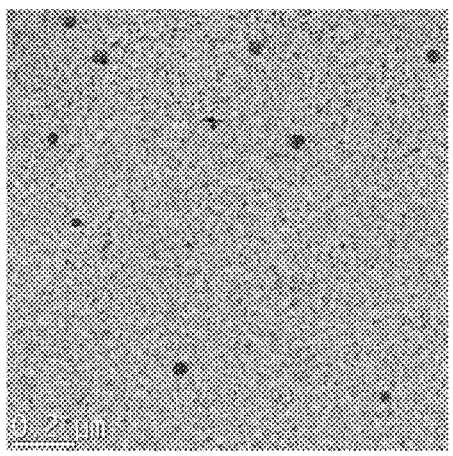
Figure 4C:
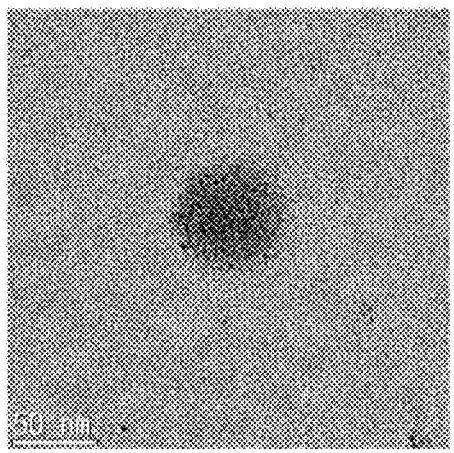

The particle size and concentration of the isolated exosomes were measured by nanoparticle tracking analysis (NTA) instrument (purchased from Malvern) or tunable resistive pulse sensing (TRPS) instrument (purchased from Izon Science). The uniformity and size of the isolated exosomes were analyzed by transmission electron microscopy (TEM). FIGS. 4A to 4C show the results of TRPS, NTA and TEM of the exosomes isolated by the isolation method according to one embodiment of the present invention.

Figure 5A:
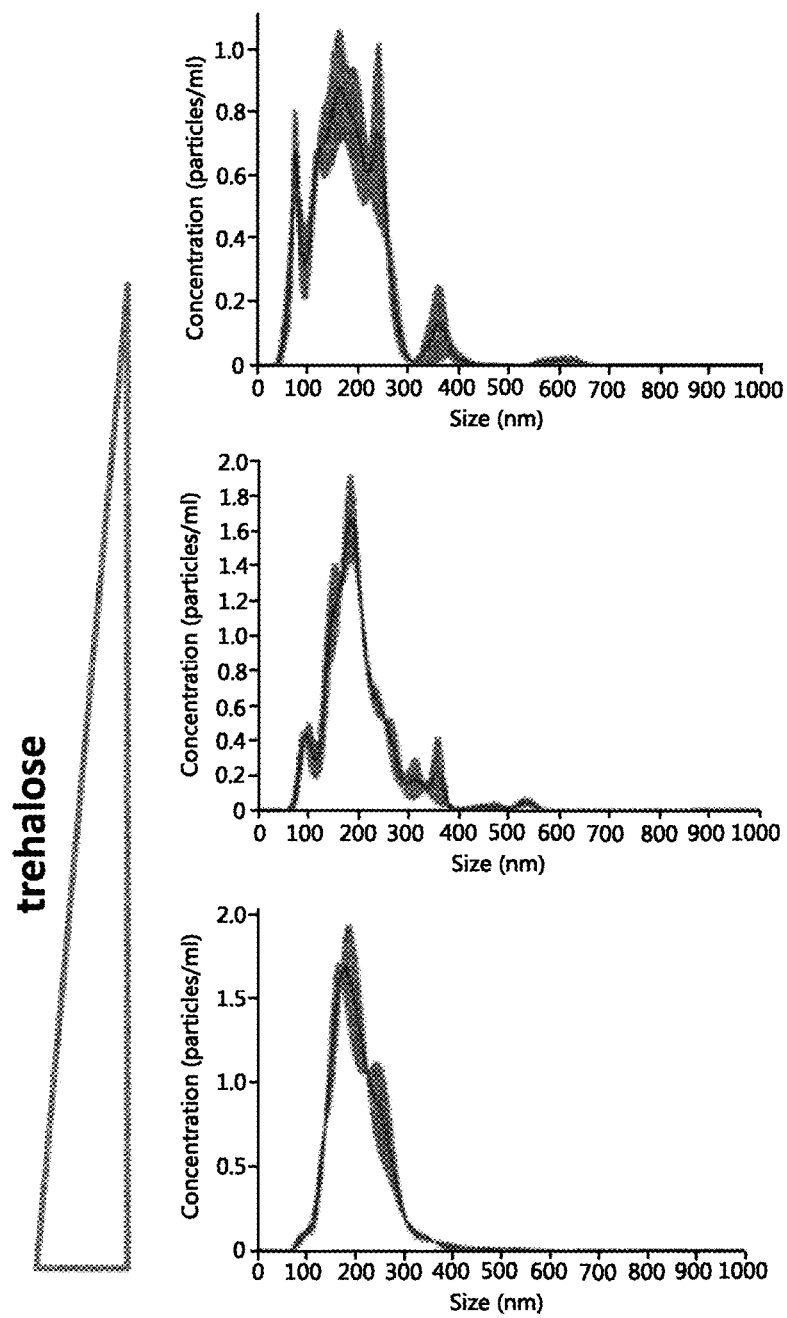
FIGS. 5A to 5C show the results of NTA analysis of particle size distributions, which indicate that exosomes having a uniform particle size distribution and high purity are obtained by the addition of trehalose. As the amount of trehalose added increases, a particle size distribution with a single peak can be obtained.
Figure 5B:
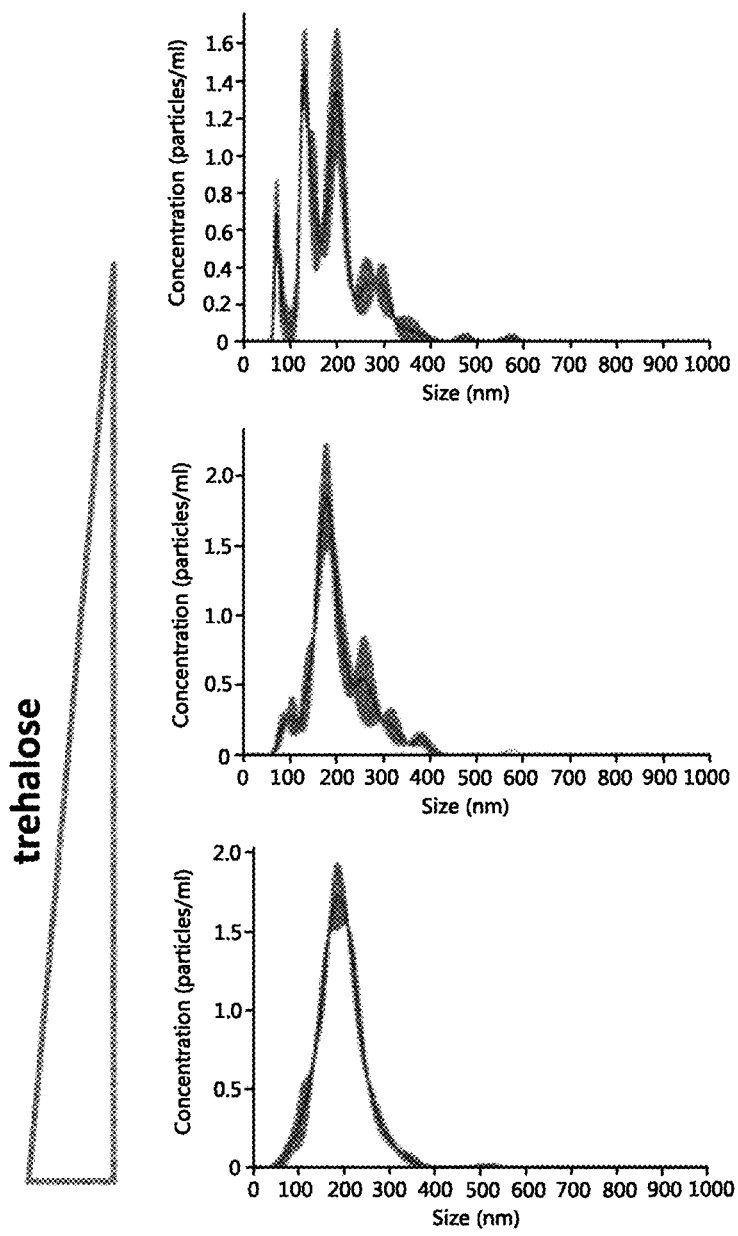
Figure 5C:
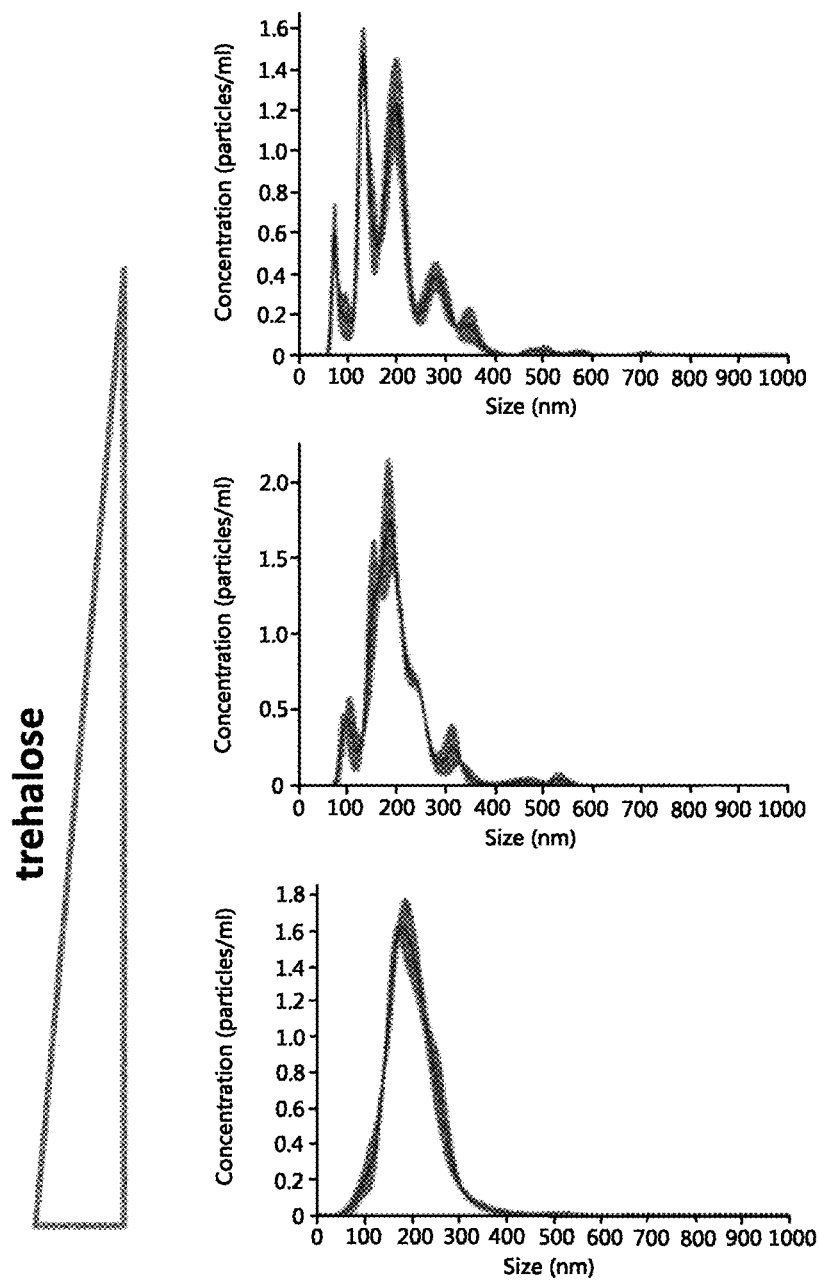

After exosomes were isolated by the TFF method, the size distribution of the exosomes was analyzed by NTA depending on whether trehalose was added. The results of the analysis are shown in FIGS. 5A to 5C. The concentration of trehalose was increased from 0 wt % to 1 wt % and 2 wt % (from the top to the bottom in FIGS. 5A to 5C), and the experiment was repeated three times. It was confirmed that when no trehalose was used, particles having a size of 300 nm or more were observed, whereas as the amount of trehalose added was increased, the number of particles having a size of 300 nm or more decreased and the size distribution of the exosomes became uniform.

Figure 6A:
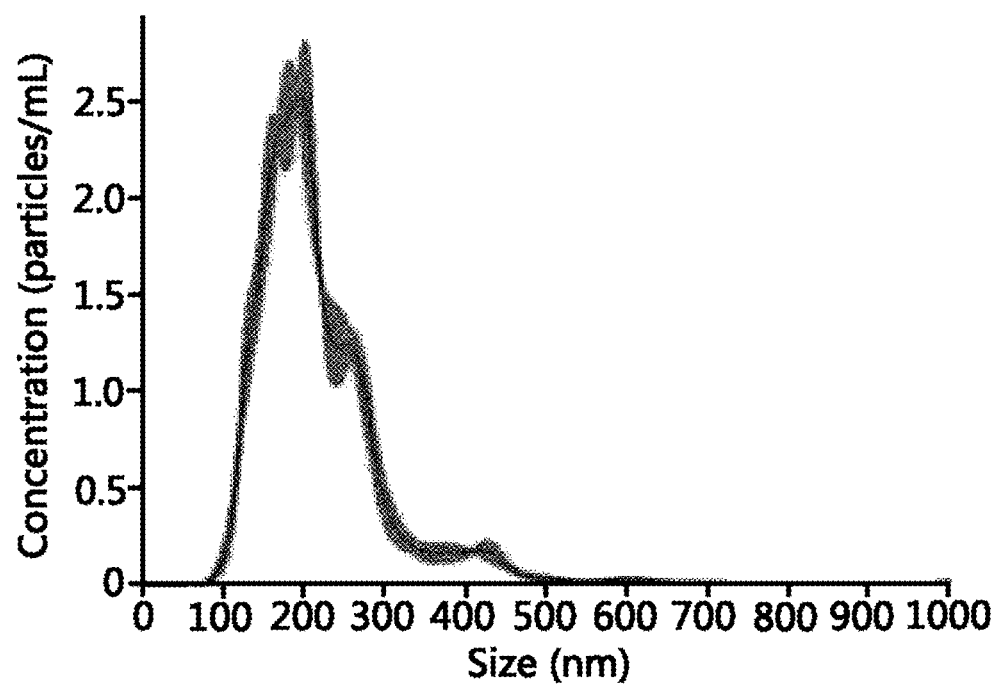
FIGS. 6A to 6C show the results of NTA analysis that indicate particle size distributions obtained depending on whether or not trehalose was added in a process of preparing exosomes according to one embodiment of the present invention.
Figure 6B:
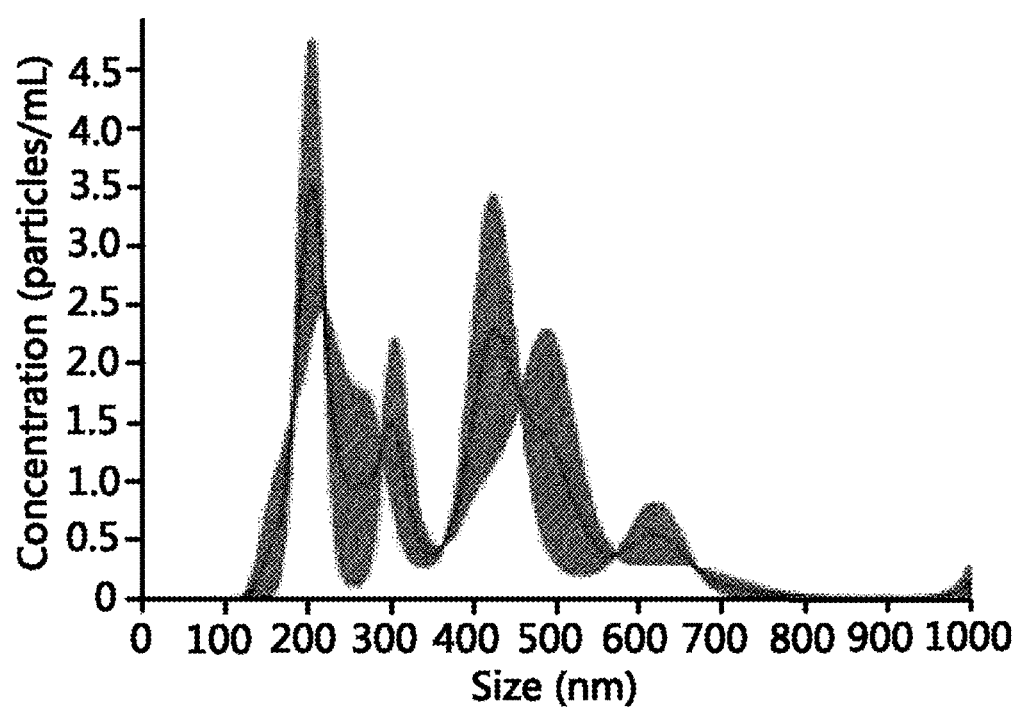
Figure 6C:
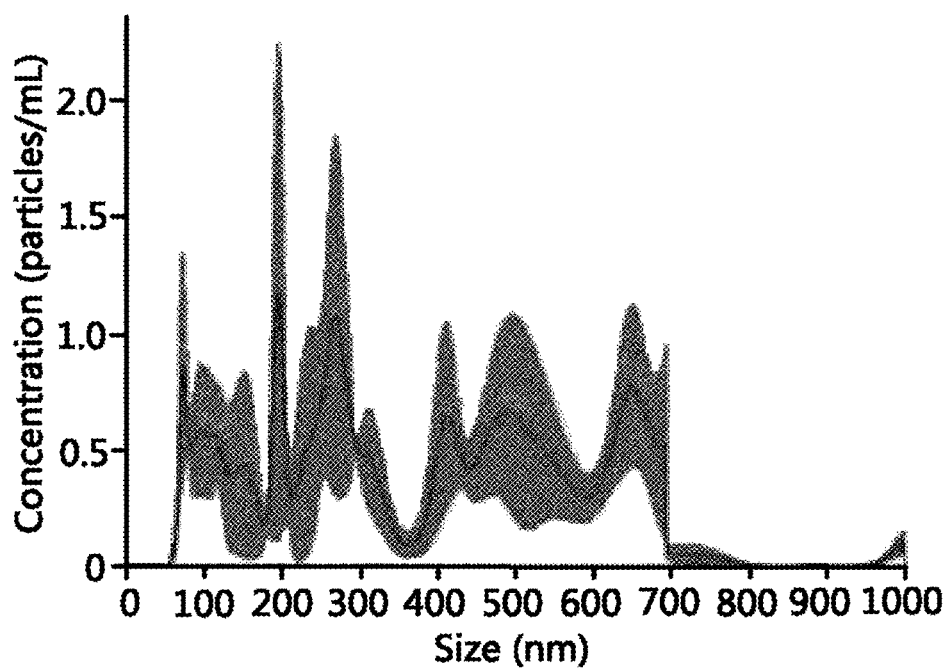

The effect due to the addition of trehalose in the process of isolating exosomes by the TFF method was additionally examined. As shown in FIGS. 6A to 6C, when 2 wt % trehalose in PBS was added throughout the process of preparing exosomes, exosomes having a uniform size distribution could be obtained (FIG. 6A). However, when the conditioned medium, which had been freeze-stored without adding trehalose, was used, but the TFF process was performed with adding trehalose only in the diafiltration process, or the TFF process was performed without adding any trehalose, uneven exosomes including a large amount of large particles were obtained (FIGS. 6B and 6C).

Figure 6D:
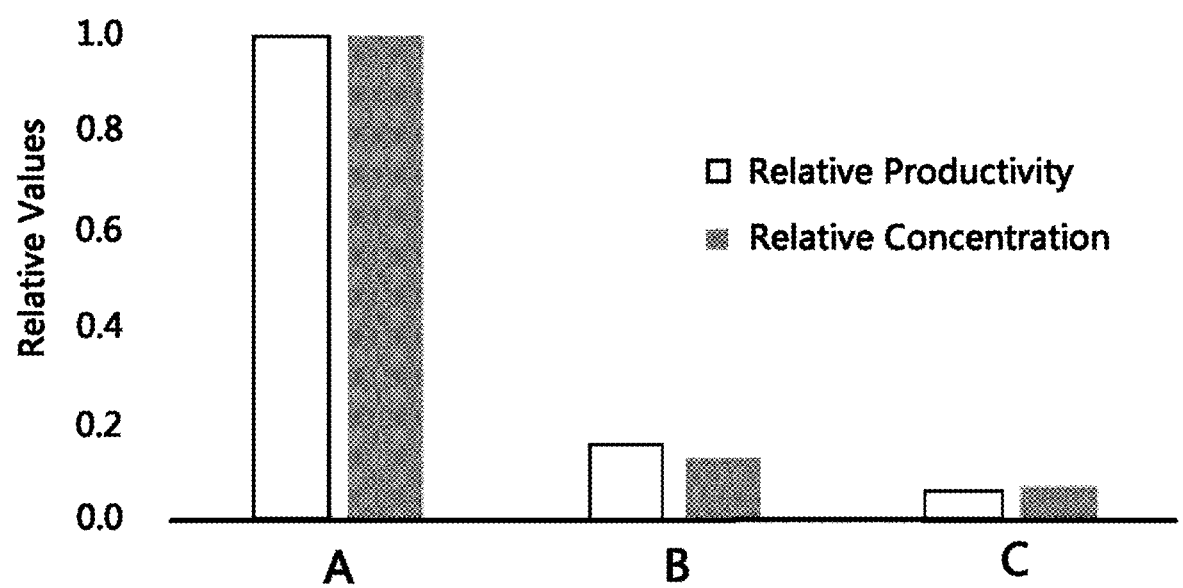
"FIG. 6D" shows the results of comparing the relative productivity and relative concentration of exosomes isolated by the methods of FIGS. 6A to 6C.
Figure 6E:
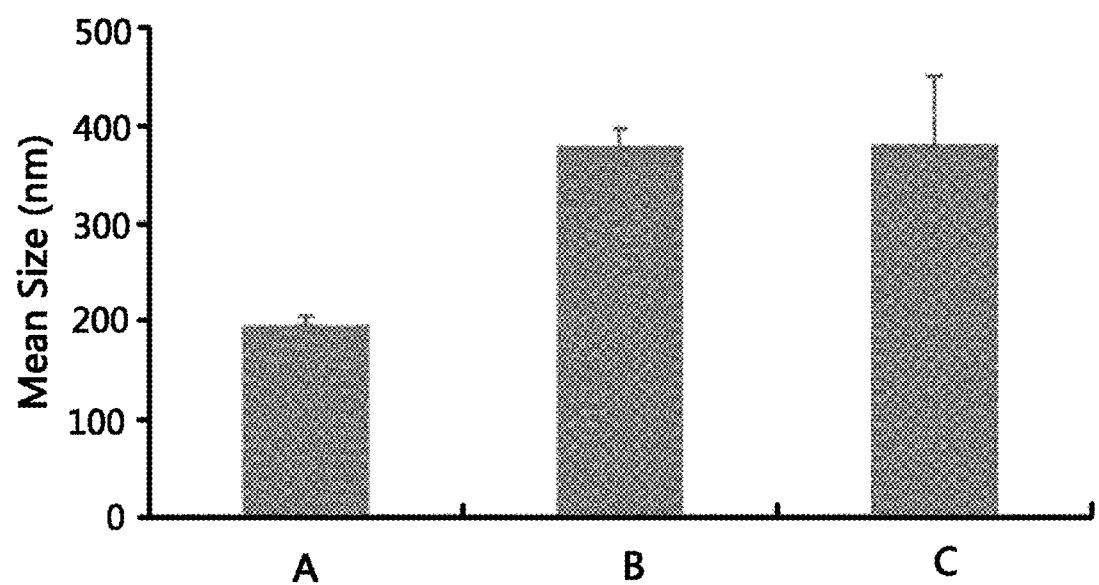
"FIG. 6E" shows the mean size of exosomes isolated by the methods of FIGS. 6A to 6C.

The relative productivity and concentration of the isolated exosomes were compared, and as a result, exosomes could be obtained with very high productivity when trehalose was added throughout the exosome production process. The obtained exosomes were at least 5 times concentration of the control (in which trehalose was not added throughout the exosome production process) (FIG. 6D). As shown in the NTA analysis result, it was confirmed that the mean size of the isolated exosomes was uniform (200 nm) when trehalose was added throughout the exosome production process (FIG. 6E).

Figure 4D:
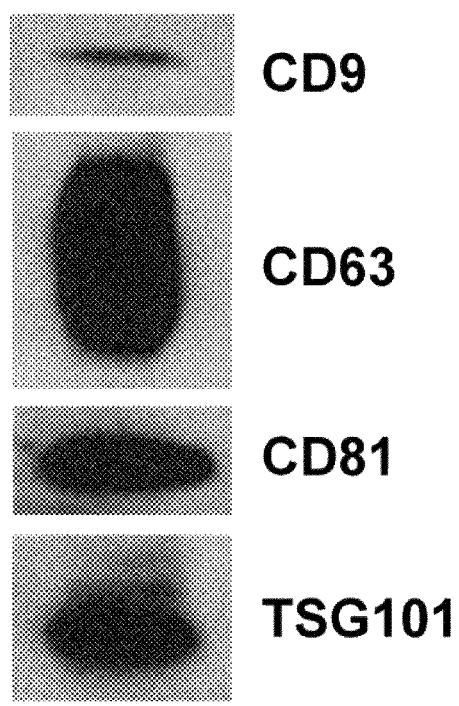

FIG. 4D shows the results of Western blot analysis of the exosomes isolated by the isolation method according to one embodiment of the present invention. As shown therein, the presence of CD9, CD63, CD81 and TSG101 markers was confirmed. As antibodies for each of the markers, anti-CD9 (purchased from Abcam), anti-CD63 (purchased from System Biosciences), anti-CD81 (purchased from System Biosciences), and anti-TSG101 (purchased from Abcam) were used, respectively.

Figure 4E:
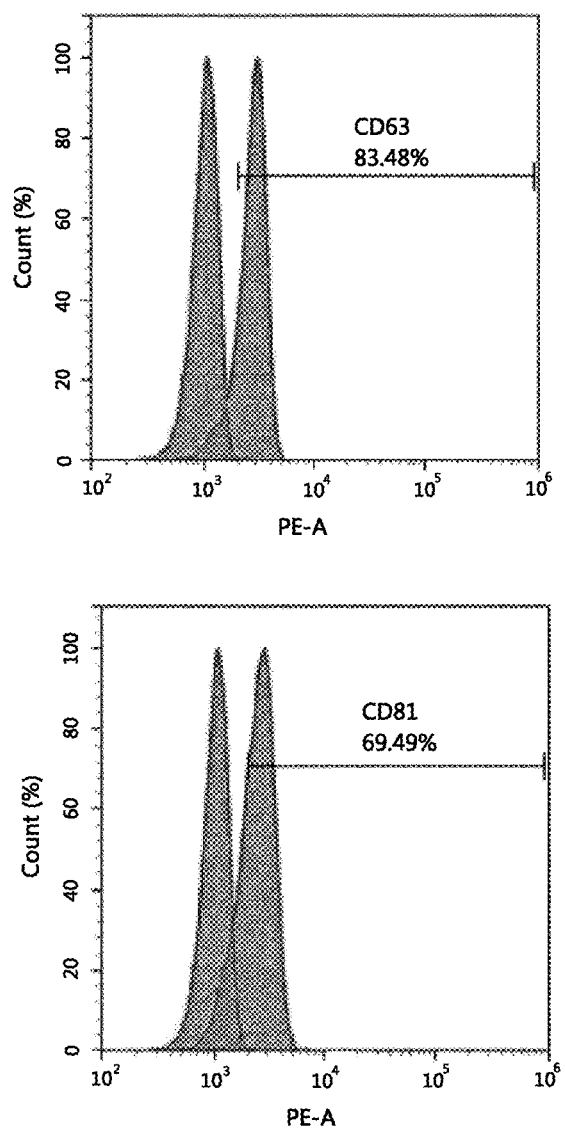

FIG. 4E shows the results of flow cytometry of the exosomes isolated by the isolation method according to one embodiment of the present invention. As shown therein, the presence of CD63 and CD81 markers was confirmed. To isolate CD63-positive exosomes, an Exosome-Human CD63 Isolation/Detection Reagent kit (purchased from ThermoFisher Scientific) was used according to the manufacturer's instruction. The markers were stained with PE-Mouse anti-human CD63 (purchased from BD) or PE-Mouse anti-human CD81 (purchased from BD), and then analyzed using a flow cytometer (ACEA Biosciences).

Taking the above results together, it could be confirmed that the isolation method according to one embodiment of the present invention could economically and efficiently isolate and purify exosomes having a uniform particle size distribution and high purity in high yield by adding trehalose in the manufacturing process based on tangential flow filtration. In addition, it could be seen that the processes of the isolation method according to one embodiment of the present invention can be scaled-up and are also suitable for GMP.

Example 4: Measurement of Cytotoxicity Following Exosome Treatment

In order to evaluate the cytotoxicity of exosomes, isolated by the isolation method according to one embodiment of the present invention, in human dermal fibroblast HS68 cells, the cells were treated with various concentrations of the exosomes, and the proliferation rate of the cells was examined. HS68 cells were suspended in 10% FBS-containing DMEM, and then seeded and grown to 80 to 90% confluency and cultured in an incubator at 37° C. under 5% $CO_2$ for 24 hours. After 24 hours, the medium was removed, and the cells were treated with various concentrations of the exosomes prepared in Example 2. Then, the viability of the cells was evaluated while the cells were cultured for 24 to 72 hours. The cell viability was measured using WST-1 reagent (purchased from Takara), MTT reagent (purchased from Sigma), CellTiter-Glo reagent (purchased from Promega) or alamarBlue reagent (purchased from ThermoFisher Scientific) with a microplate reader (purchased from Molecular Devices).

Figure 7:
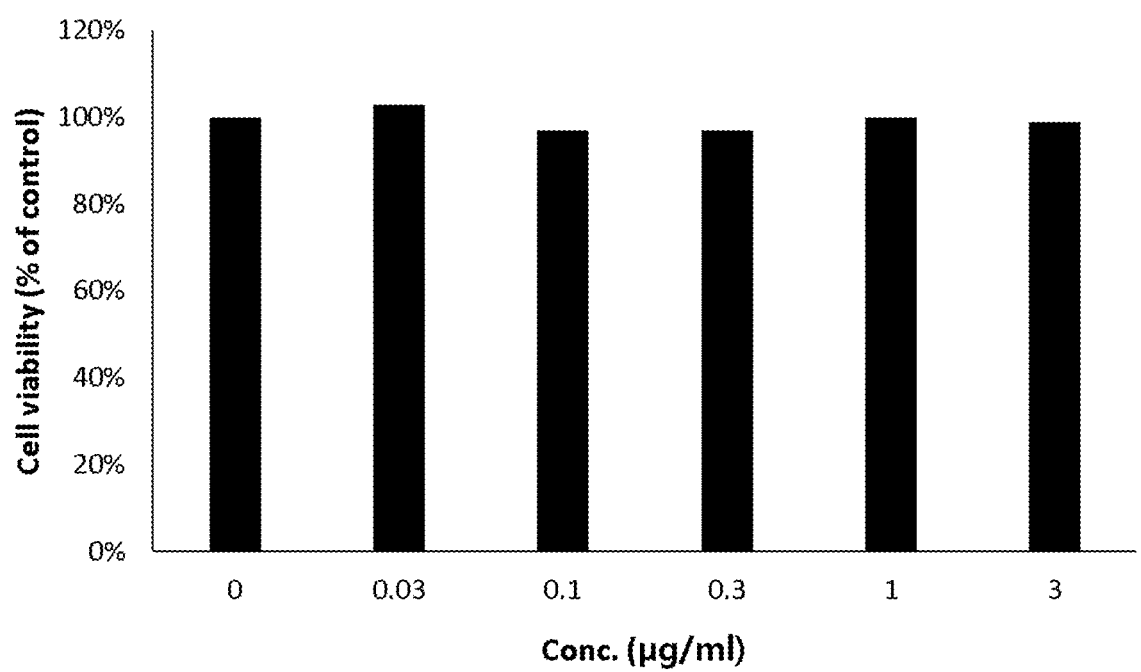
FIG. 7 shows the results indicating that exosomes according to one embodiment of the present invention were not cytotoxic when human fibroblast HS68 cells were treated with the exosomes.

As a control, the cells cultured in conventional cell culture medium not treated with the exosomes was used. It was confirmed that the exosomes of the present invention showed no cytotoxicity in the concentration range used in the test (FIG. 7).

Example 5: Preparation of Combination of Sapogenin and Exosomes

The combination of sapogenin and exosomes was prepared as follows and used:

(1) Sapogenin and exosomes were mixed and incubated at room temperature, and the reaction product was used intact ("sapogenin-exosome mixture"); and (2) Sapogenin and exosomes were mixed and incubated at room temperature, and the reaction product was used after removing sapogenin that did not penetrate into the exosomes ("sapogenin-exosome"). To remove sapogenin that was not associated with the exosomes, a size exclusion column, for example, MW 3000 spin column (purchased from ThermoFisher), was used.

As an example, not limiting the present invention, diosgenin was used as sapogenin.

Hereinafter, both (1) and (2) above will be referred to as the combination of sapogenin and exosomes.

Example 6: Evaluation of Lipid Uptake for Induction of Adipogenesis

A sufficient number of 3T3-L1 preadipocytes were obtained by clonal expansion and used. For the induction of adipogenesis of 3T3-L1 preadipocytes, the amount of accumulation of lipids in the cells resulted from the combination of sapogenin and exosomes was evaluated as follows.

3T3-L1 preadipocytes were seeded into each well of a 24-well plate at a density of $8 \times 10^3$ cells/cm$^2$, and then cultured in an incubator at 37° C. under 5% $CO_2$ for 3 to 4 days. Next, the 3T3-L1 cells were cultured and induced into differentiation for 2 days in DMEM medium (hereinafter, referred to as "differentiation medium") containing 10% FBS (fetal bovine serum) and 5% penicillin/streptomycin, which is supplemented with 0.5 mM IBMX (purchased from Sigma), 0.5 µM dexamethasone (purchased from Sigma) and 5 µg/mL of insulin (purchased from Sigma) (hereinafter, referred to as "differentiation cocktail").

Test groups were divided according to the differentiation conditions used for induction of differentiation as follows:

(1) Negative control: a group cultured in differentiation medium;

(2) Pioglitazone: a group (positive control) (denoted by "P" in FIG. 10) cultured in differentiation medium along with treatment with pioglitazone (purchased from Sigma; final concentration of 10 µM);

(3) Diosgenin: a group (denoted by "D" in FIG. 10) cultured in differentiation medium along with treatment with diosgenin (purchased from Sigma; final concentration of 10 µM); and (4) Combination of diosgenin and exosomes (Diosgenin+Exosome): a group (denoted by "D+Exo" in FIG. 10) cultured in differentiation medium along with treatment with the combination of diosgenin (final concentration of 10 µM) and exosomes (final concentration of 4 µg/mL) prepared in Example 2.

2 days after culturing 3T3-L1 preadipocytes in differentiation medium to initiate the induction of differentiation, the differentiation medium for each group was replaced with DMEM medium (hereinafter, referred to as "maturation medium") containing 10% FBS (fetal bovine serum) and 5% penicillin/streptomycin, which is supplemented with 5 µg/mL of insulin, and then the cells were cultured and induced into maturation for 2 to 20 days. At this time, the maturation medium was replaced every two days.

The matured 3T3-L1 cells were washed, fixed, and then stained with Oil Red O. The amount of accumulation of lipids in the cells was quantified by image analysis. In addition, the nuclei were stained with hematoxylin to distinguish the lipid droplets accumulated in the cytoplasm from the nuclei, and then optical micrographs were taken. The lipid droplets accumulated in the cytoplasm were stained red by Oil Red O, and the nuclei were stained purple by hematoxylin (FIG. 8).

Figure 8:
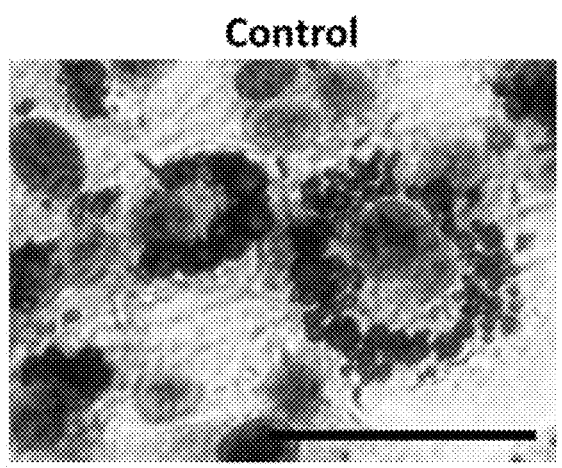
FIG. 8 shows optical micrographs showing that the treatment with the combination of sapogenin and exosomes according to one embodiment of the present invention for induction of adipogenesis of 3T3-L1 cells resulted in increases in the amount of accumulation and the size of lipid droplets in the cells.
Figure 8:
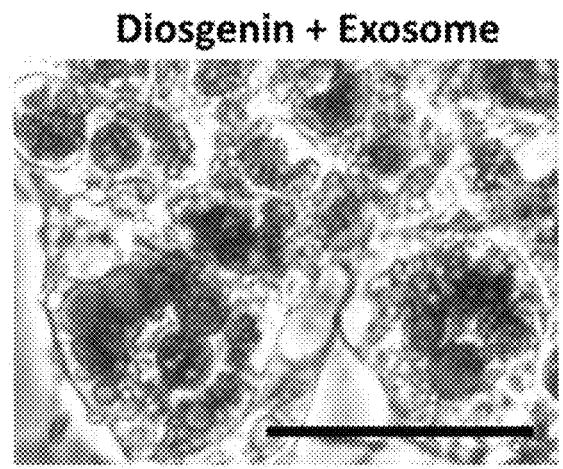

As shown in FIG. 8, it could be confirmed that for the induction of adipogenesis of 3T3-L1 cells, a much larger number of lipid droplets were accumulated in the cells treated with the combination of sapogenin (diosgenin) and exosomes according to one embodiment of the present invention, as compared with those accumulated in the negative control group treated only with the differentiation medium. The size of lipid droplets in the cells treated with the combination of sapogenin (diosgenin) and exosomes was also larger than that in the negative control group treated only with the differentiation medium.

Figure 9:
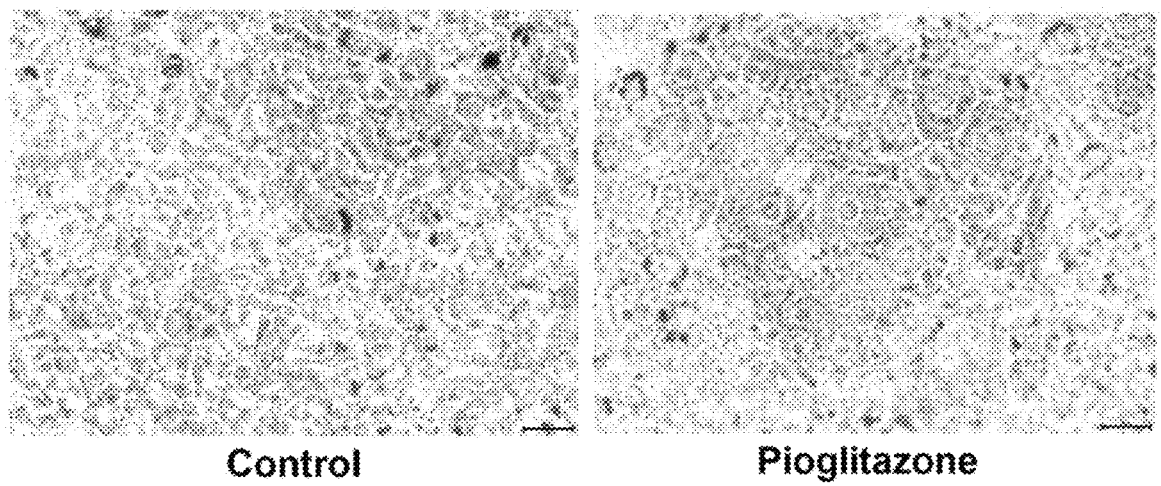
FIG. 9 shows optical micrographs obtained by staining 3T3-L1 cells with Oil Red O at 6 days after culturing 3T3-L1 cells in differentiation medium to initiate the induction of differentiation of 3 T3 -L1 cells.
Figure 10:
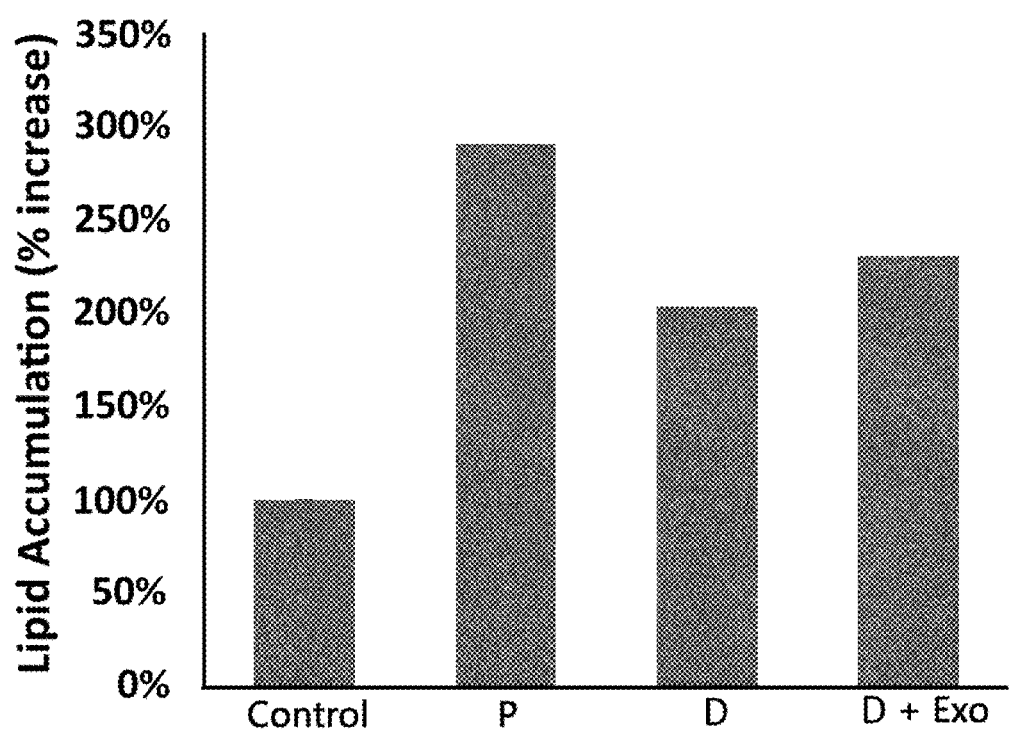
FIG. 10 is a graph showing an increase of the amount of lipid accumulation in Oil Red O-stained 3T3-L1 cells as a percentage relative to the negative control.

Meanwhile, since the formation of lipid droplets in 3T3-L1 cells is a marker indicative of adipogenesis, the measurement of the amount of accumulation of lipid droplets in 3T3-L1 cells following treatment with a specific test substance makes it possible to objectively evaluate whether the test substance has the effects of stimulating lipid accumulation and promoting adipogenesis. For this, 6 days after culturing 3T3-L1 cells in differentiation medium to initiate the induction of differentiation for each group, the 3T3-L1 cells were stained with Oil Red O and optical micrographs were taken (FIG. 9). In addition, Oil Red O dye in the stained lipid droplets was eluted with isopropanol, and then the absorbance of the eluted solution was measured at 510 nm, thereby determining the amount of accumulation of lipids in the 3T3-L1 cells for each group. Furthermore, an increase in the amount of lipid accumulation for each group relative to the negative control was evaluated as a percentage (FIG. 10).

As a result, it was confirmed that the amount of accumulation of lipids in the cells treated with the combination of sapogenin (diosgenin) and exosomes according to one embodiment remarkably increased, as compared with that in the negative control group, and also remarkably increased, as compared with that in the cells treated with sapogenin (diosgenin) alone. From these results, it can be seen that when adipogenesis of preadipocytes is induced along with treating preadipocytes with the combination of sapogenin and exosomes according to one embodiment of the present invention, the amount of accumulation of lipids in the cells remarkably increases and adipogenesis is promoted, as compared with the group treated with sapogenin alone.

Therefore, when the composition comprising the combination of sapogenin and exosomes according to the present invention is applied to a part of the body showing flaws or an area of the skin showing flaws caused by a deficit in lipids, the applied composition is able to exhibit correction of skin flaws, plumpness, volume-up and skin tightening effects by increasing the amount of lipid accumulation.

Example 7: Evaluation of Cytoprotective Effect for Induction of Adipogenesis It is known that sapogenin can induce cell death at a high concentration. In order to evaluate the cytoprotective effect of the combination of sapogenin and exosomes according to one embodiment of the present invention, the adipogenesis of 3T3-L1 preadipocytes was induced in the same manner as Example 6, and the cell viability was evaluated. Test groups were divided according to the differentiation conditions used for induction of differentiation as follows:

(1) Negative control: a group cultured in differentiation medium;

(2) Diosgenin: a group (denoted by "D" in FIG. 12) cultured in differentiation medium along with treatment with a high concentration of diosgenin (final concentration of 30 µM); and (3) Combination of diosgenin and exosomes (Diosgenin+ Exosome): a group (denoted by "D+Exo" in FIG. 12) cultured in differentiation medium along with treatment with the combination of a high concentration of diosgenin (final concentration of 30 µM) and exosomes (final concentration of 4 µg/mL) prepared in Example 2.

Figure 11:
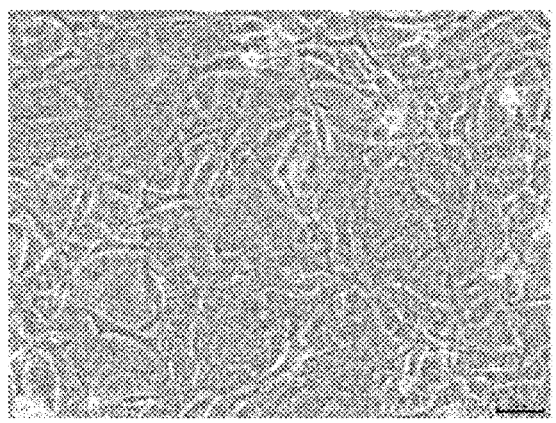
FIG. 11 shows optical micrographs obtained at 3 days after culturing 3T3-L1 cells in differentiation medium to initiate the induction of differentiation of 3T3-L1 cells.
Figure 11:
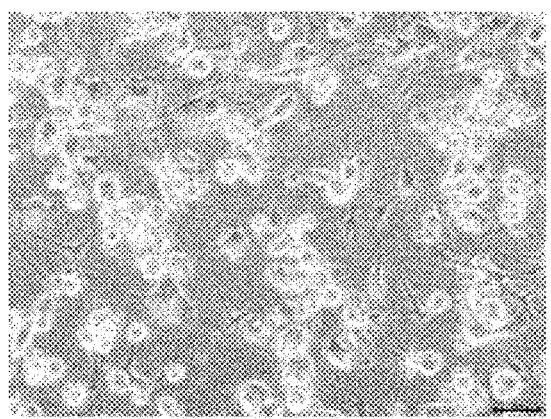
Figure 11:
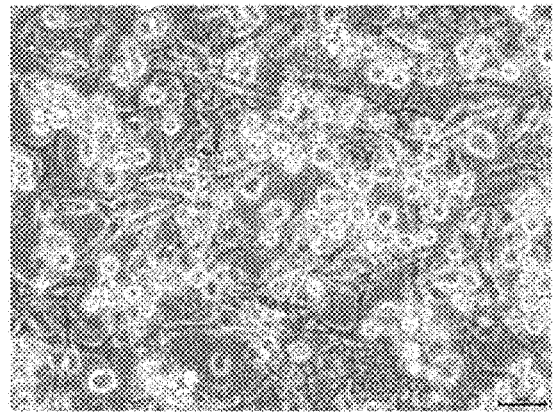
Figure 12:
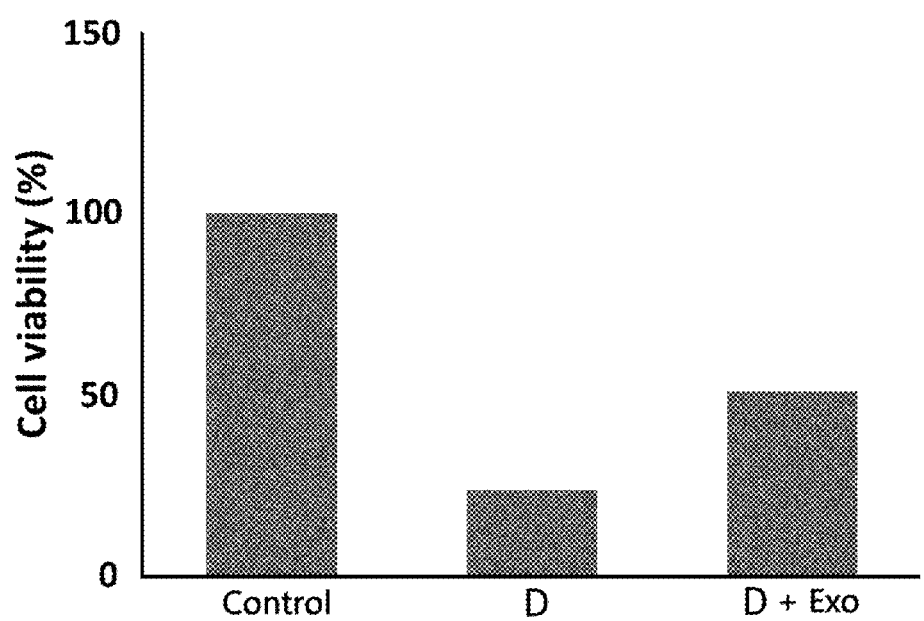
FIG. 12 is a graph showing the results of cell viability as a percentage relative to the negative control obtained by performing an MTT assay at 3 days after culturing 3T3-L1 cells in differentiation medium to initiate the induction of differentiation of 3T3-L1 cells.

3 days after culturing 3T3-L1 cells in differentiation medium to initiate the induction of differentiation according to the method of Example 6, the photographs of the 3T3-L1 cells for each group were taken with an optical microscope. As shown in FIG. 11, it was observed that in the group treated only with a high concentration of sapogenin (diosgenin), the cell death of 3T3-L1 cells occurred and thus there were many 3T3-L1 cells which lost their original shape, and detached from the bottom and floated in the medium. In contrast, when 3T3-L1 cells were treated with the combination of a high concentration of sapogenin (diosgenin) and exosomes according to one embodiment of the present invention, the relatively low cell death of the 3T3-L1 cells was observed. In addition, in order to quantitatively evaluate the observed results, the cell viability was measured by performing an MTT assay. 3 days after culturing 3T3-L1 cells in differentiation medium to initiate the induction of differentiation for each group, an MTT assay was performed using 0.5 mg/mL of thiazolyl blue tetrazolium bromide. The absorbance was measured at 570 nm and the cell viability of each group relative to the negative control group was evaluated as a percentage (FIG. 12).

As a result, it was confirmed that when the cells were treated with the combination of a high concentration of sapogenin (diosgenin) and exosomes according to one embodiment of the present invention, the cell viability remarkably increased, as compared with that in the group treated with a high concentration of sapogenin (diosgenin) alone. It can be seen that when adipogenesis of preadipocytes was induced along with treating preadipocytes with the combination of sapogenin and exosomes according to one embodiment of the present invention, the amount of lipid uptake into the cells increased, as compared with that in the group treated with sapogenin alone, and the cells were protected from the cytotoxicity caused by a high concentration of sapogenin.

Therefore, the composition comprising the combination of sapogenin and exosomes according to the present invention is able to increase lipid uptake into adipocytes and to promote adipogenesis as compared with the sapogenin alone, and also exhibit correction of skin flaws, plumpness, volume-up and skin tightening effects while decreasing side effects on the skin by reducing the cytotoxicity caused by sapogenin.

Example 8: Evaluation of Adipogenesis-Promoting Effect by Measurement of Expression Levels of Adipogenesis Markers The adipogenesis-promoting effect of the combination of sapogenin and exosomes according to one embodiment of the present invention was evaluated as follows.

3T3-L1 preadipocytes were suspended in DMEM medium (Dulbecco Modified Eagle Medium) (purchased from ThermoFisher Scientific) supplemented with 10% NBCS (newborn calf serum) and 1% penicillin-streptomycin. Next, the cells were seeded into each well of a 12-well plate at a density of $8 \times 10^3$ cells/cm$^2$, and then cultured in an incubator at 37° C. under 5% $CO_2$ for 72 hours. Thereafter, the 3T3-L1 cells were cultured and induced into differentiation for 48 hours in DMEM medium (hereinafter, referred to as "differentiation medium") containing 10% FBS (fetal bovine serum) and 1% penicillin/streptomycin, which is supplemented with 0.5 mM IBMX (purchased from Sigma), 0.5 µM dexamethasone (purchased from Sigma) and 5 µg/mL of insulin (purchased from Sigma) (hereinafter, referred to as "differentiation cocktail"). Test groups were divided according to the differentiation conditions used for induction of differentiation as follows:

(1) Growth medium: a group cultured in DMEM medium in place of differentiation medium;

(2) Differentiation medium: a group cultured in differentiation medium;

(3) Pioglitazone: a group (a positive control) cultured in differentiation medium along with treatment of pioglitazone (final concentration of 10 µM); and (4) Combination of diosgenin and exosomes (Diosgenin+ Exosome): a group cultured in differentiation medium along with treatment with the combination of diosgenin (final concentration of 10 µM) and exosomes (final concentration of 6 µg/mL) prepared in Example 2.

48 hours after culturing 3T3-L1 preadipocytes in differentiation medium to initiate the induction of differentiation, the differentiation medium for each group was replaced with DMEM medium (hereinafter, referred to as "maturation medium") containing 10% FBS (fetal bovine serum) and 1% penicillin/streptomycin, which is supplemented with 5 µg/mL of insulin, and then the cells were cultured for 48 hours to be induced into maturation.

0, 1, 4 and 6 days after culturing 3T3-L1 cells in differentiation medium to initiate the induction of differentiation, the expression levels of adipogenesis-related markers for each group were measured by real-time PCR to confirm the adipogenesis-promoting effect of the combination of sapogenin (diosgenin) and exosomes according to one embodiment of the present invention. cDNA was synthesized from RNA isolated from the 3T3-L1 cells of each group, and the mRNA expression levels of PPAR-γ (peroxisome proliferator-activated receptor gamma), C/EBP-α (CCAAT/enhancer-binding protein alpha), FAS (fatty acid synthase), ACC (acetyl-CoA carboxylase), GDPH (glycerol-3-phosphate dehydrogenase), GADPH (glyceraldehyde-3-phosphate dehydrogenase) and Pref-1 (preadipocyte factor 1), which are adipogenesis-related markers, were measured by a real-time PCR method. The mRNA expression levels for each group were compared with those of the other groups. As a reference gene for normalizing the above genes, PPIA (peptidylprolyl isomerase A) gene was used. The sequences of primers used in real-time PCR are shown in Table 1 below.

TABLE 1

Nucleotide sequences of primers used in real-time PCR

| Genes | Forward primer (5'→ 3') | Reverse primer (5'→ 3') |
|---|---|---|
| Pref-1 | TGCACACTGGGTTCTCTGG (SEQ ID NO: 1) | ATCGTAGCCGCAACCAACAG (SEQ ID NO: 2) |
| PPAR-γ | GGAGCCTAAGTTTGAGTTTGCTGTG (SEQ ID NO: 3) | TGCAGCAGGTTGTCTTGGATG (SEQ ID NO: 4) |
| C/EBP-α | CAGCTTACAACAGGCCAGGTTTC (SEQ ID NO: 5) | GCTGGCGACATACAGTACACACAA (SEQ ID NO: 6) |
| FAS | TTGCTGGCACTACAGAATGC (SEQ ID NO: 7) | AACAGCCTCAGAGCGACAAT (SEQ ID NO: 8) |
| ACC | GCGTCGGGTAGATCCAGTT (SEQ ID NO: 9) | CTCAGTGGGGCTTAGCTCTG (SEQ ID NO: 10) |
| GPDH | GGCAAGATCTGTGACCAGCT (SEQ ID NO: 11) | ATCAGCACGCTCATGGGAAT (SEQ ID NO: 12) |
| GAPDH | CTTTGGTATCGTGGAAGGACTC (SEQ ID NO: 13) | GTAGAGGCAGGGATGATGTTCT (SEQ ID NO: 14) |
| PPIA | ATCTTGTCCATGGCAAATGCTG (SEQ ID NO: 15) | AAACGCTCCATGGCTTCCAC (SEQ ID NO: 16) |

Figure 13:
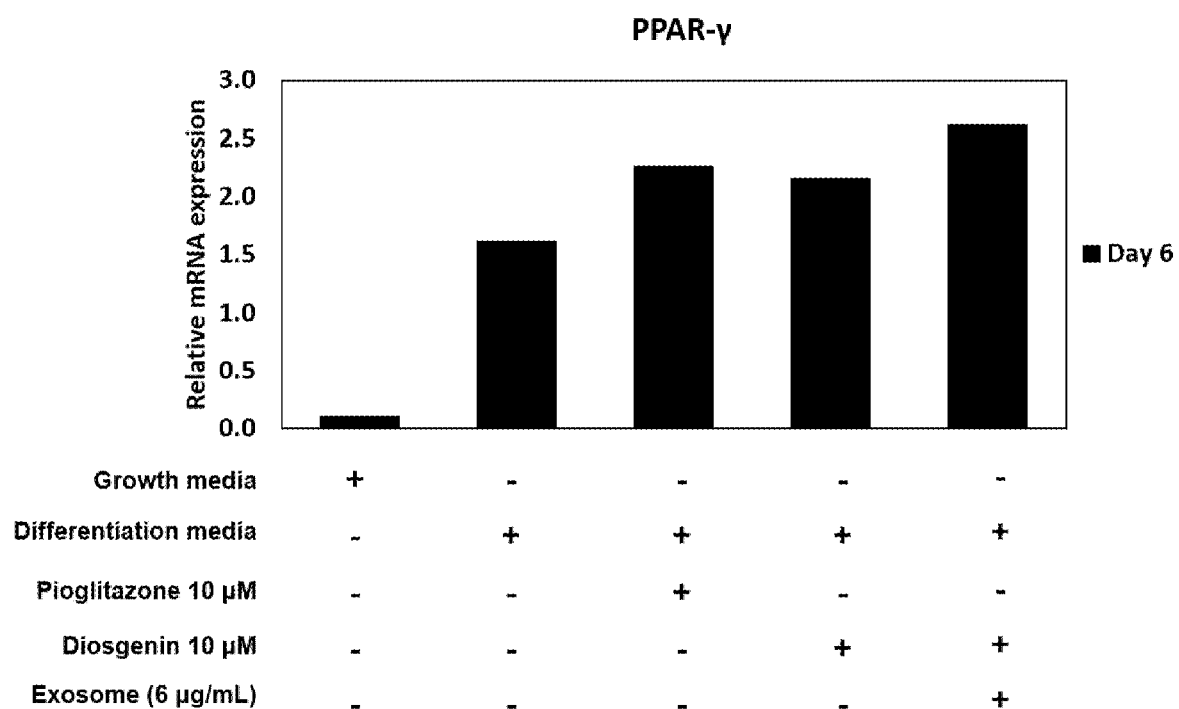
FIG. 13 is a graph showing the results of real-time PCR performed on PPAR-γ gene at 6 days after culturing 3T3-L1 cells in differentiation medium to initiate the induction of differentiation of 3T3-L1 cells.

As a result, 6 days after initiating the induction of differentiation, the treatment with the combination of sapogenin (diosgenin) and exosomes according to one embodiment of the present invention remarkably increased the mRNA expression level of the adipogenesis marker PPAR-γ, as compared with the treatment with differentiation medium alone (FIG. 13). In particular, 6 days after initiating the induction of differentiation, the treatment with the combination of sapogenin (diosgenin) and exosomes according to one embodiment of the present invention increased the mRNA expression level of PPAR-γ, as compared with the treatment with pioglitazone which is a positive control, or the treatment with diosgenin alone. Therefore, it could be confirmed that when preadipocytes were treated with the combination of sapogenin and exosomes according to one embodiment of the present invention, the combination exhibited a superior adipogenesis-promoting effect to pioglitazone at a certain time point after the induction of adipogenesis.

Figure 14:
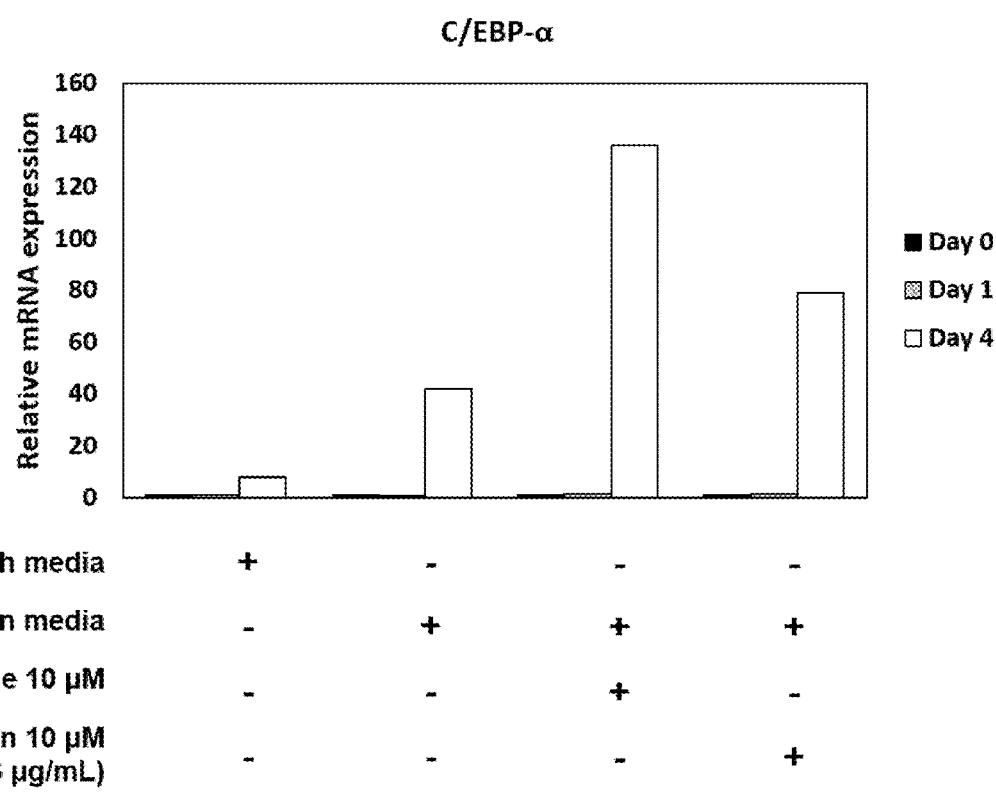
FIG. 14 is a graph showing the results of real-time PCR performed on C/EBP-α gene at 0, 1 and 4 days after culturing 3T3-L1 cells in differentiation medium to initiate the induction of differentiation of 3T3-L1 cells.
Figure 15:
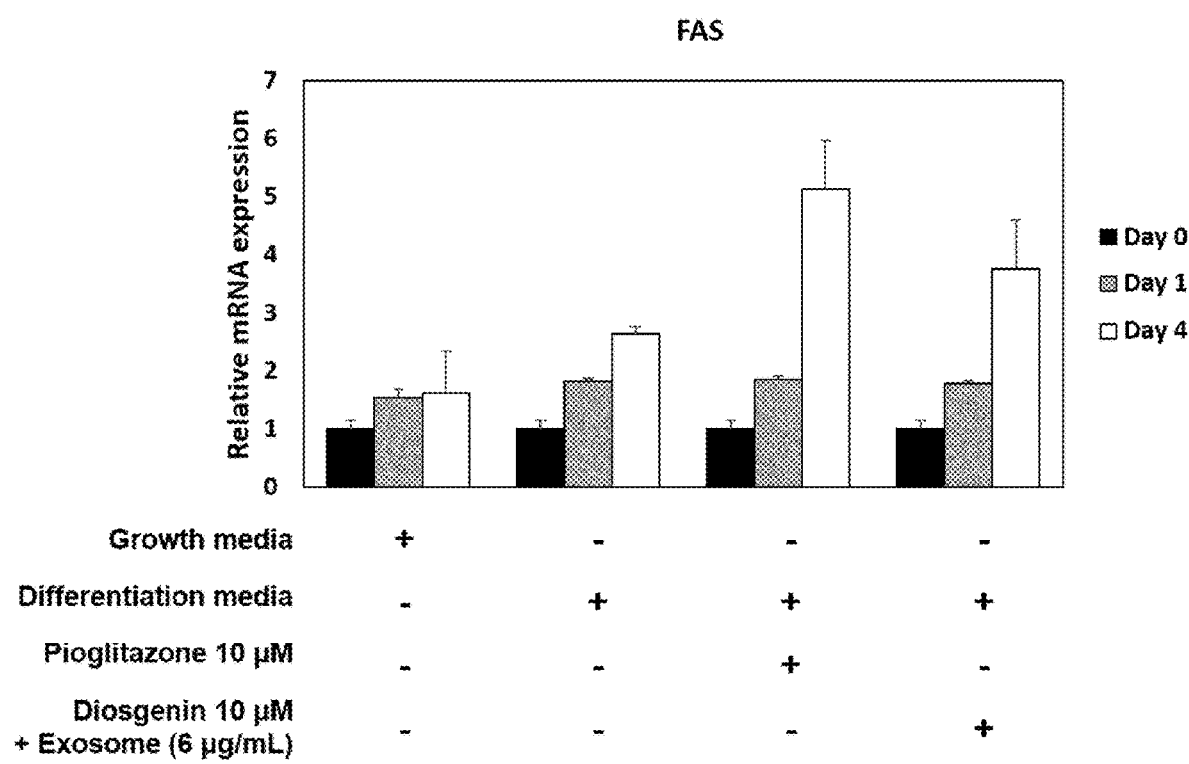
FIG. 15 is a graph showing the results of real-time PCR performed on FAS gene at 0, 1 and 4 days after culturing 3T3-L1 cells in differentiation medium to initiate the induction of differentiation of 3T3-L1 cells.
Figure 16:
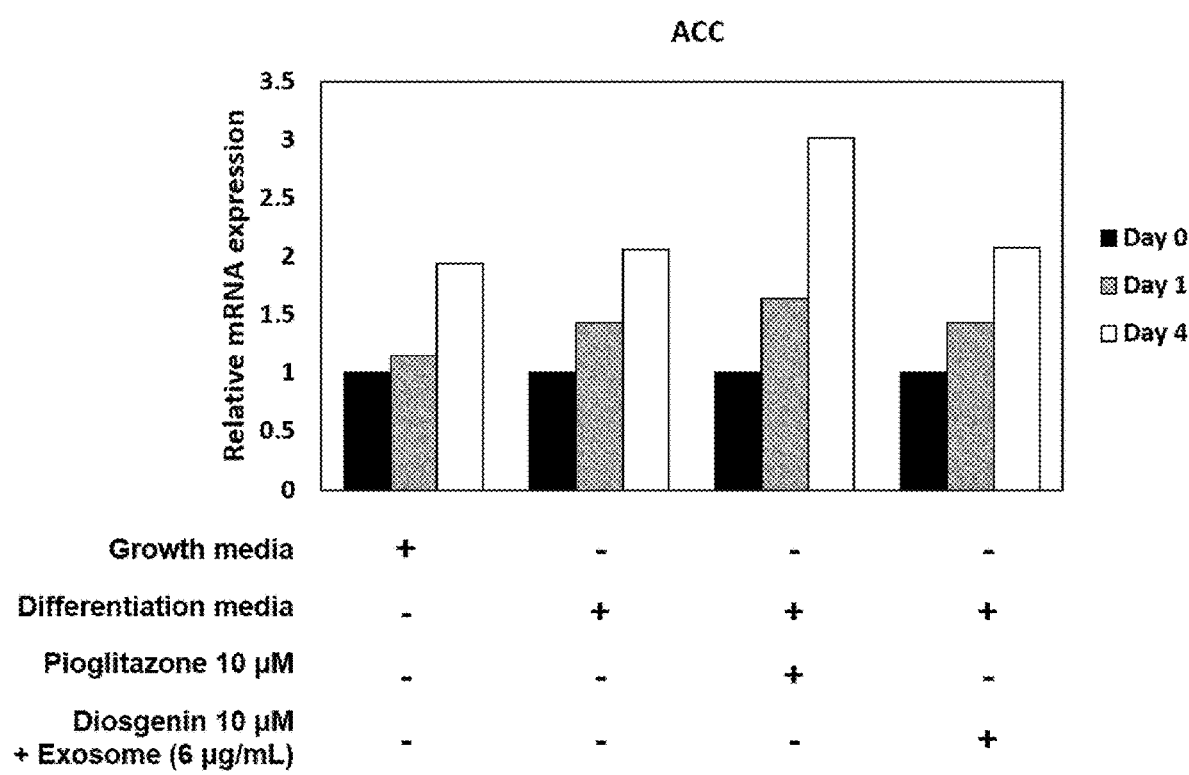
FIG. 16 is a graph showing the results of real-time PCR performed on ACC gene at 0, 1 and 4 days after culturing 3T3-L1 cells in differentiation medium to initiate the induction of differentiation of 3T3-L1 cells.
Figure 17:
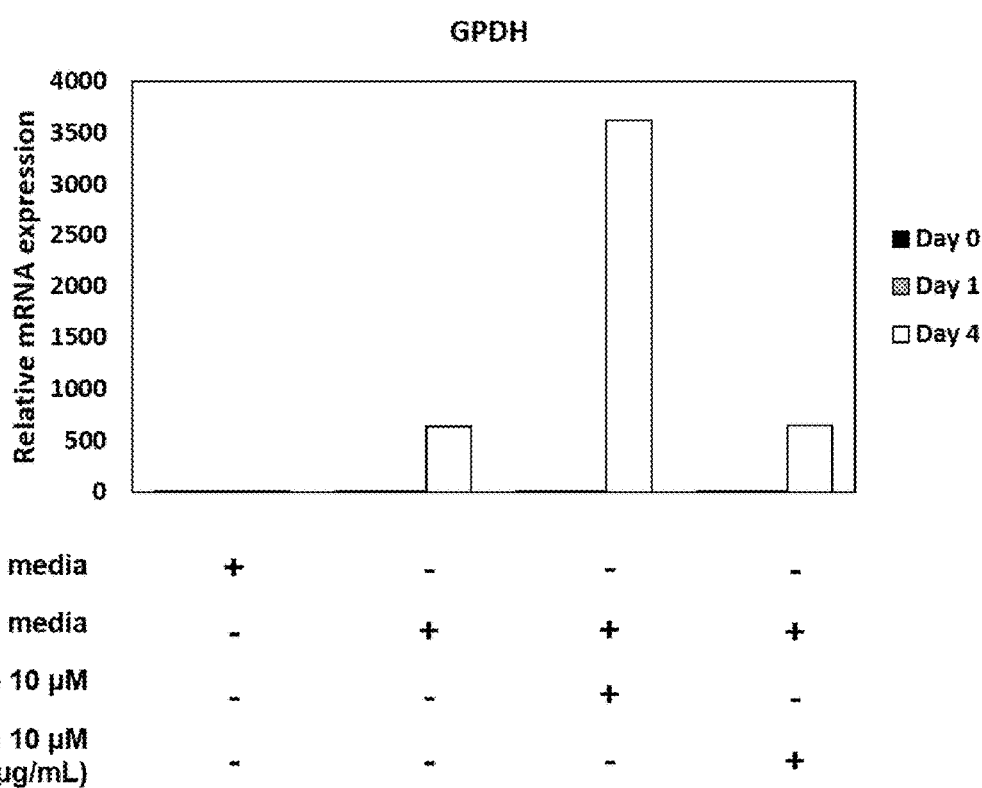
FIG. 17 is a graph showing the results of real-time PCR performed on GPDH gene at 0, 1 and 4 days after culturing 3T3-L1 cells in differentiation medium to initiate the induction of differentiation of 3T3-L1 cells.
Figure 18:
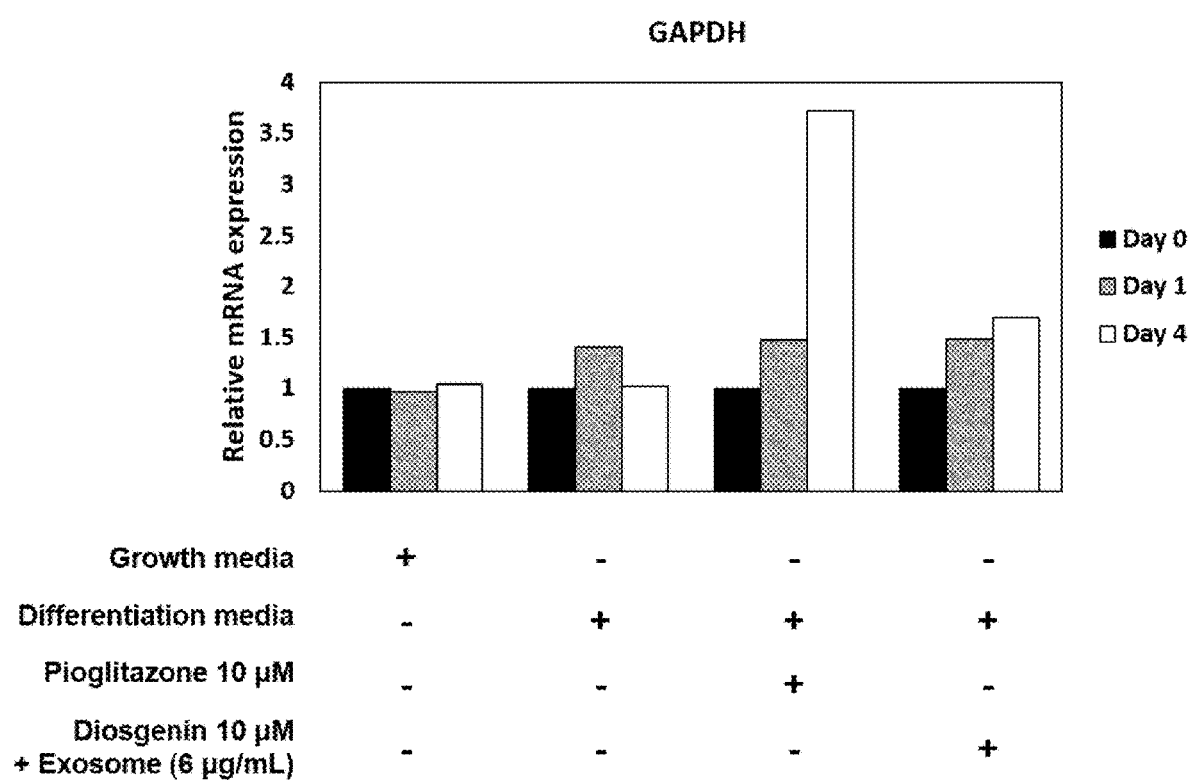
FIG. 18 is a graph showing the results of real-time PCR performed on GAPDH gene at 0, 1 and 4 days after culturing 3T3-L1 cells in differentiation medium to initiate the induction of differentiation of 3T3-L1 cells.

In addition, 4 days after initiating the induction of differentiation, the treatment with the combination of sapogenin (diosgenin) and exosomes according to one embodiment of the present invention remarkably increased the mRNA expression level of C/EBP-α (a marker present in mature adipocyte), as compared with the treatment with differentiation medium alone (FIG. 14). Furthermore, the treatment with the combination of sapogenin (diosgenin) and exosomes according to one embodiment of the present invention increased the mRNA expression levels of FAS, ACC, GDPH and GADPH, which are adipogenesis-related markers, over time after initiating the induction of differentiation (FIGS. 15 to 18).

Figure 19:
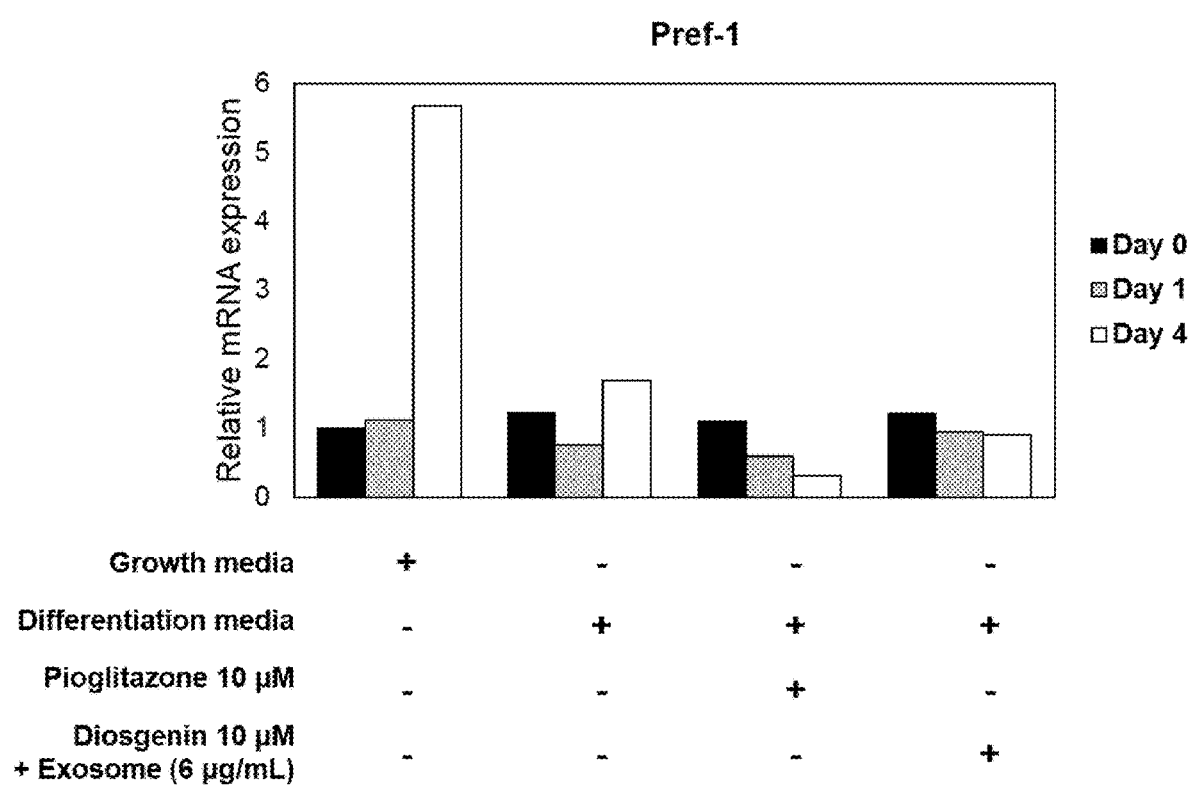
FIG. 19 is a graph showing the results of real-time PCR performed on Pref-1 gene at 0, 1 and 4 days after culturing 3T3-L1 cells in differentiation medium to initiate the induction of differentiation of 3 T3 -L1 cells.

Meanwhile, it was confirmed that the treatment with the combination of sapogenin (diosgenin) and exosomes according to one embodiment of the present invention remarkably decreased the mRNA expression level of Pref-1 (preadipocyte factor 1) which is a maker of preadipocyte (FIG. 19).

From the above-described experimental results, it can be seen that the composition comprising the combination of sapogenin and exosomes according to the present invention has the effect of promoting adipogenesis from preadipocytes to adipocytes. Thus, when the composition of the present invention is topically applied to a part of the body showing flaws or an area of the skin showing flaws caused by a deficit in lipids, it is able to promote adipogenesis and stimulate the introduction and growth of adipocytes, thereby preventing, alleviating, ameliorating or recovering a part of the body showing flaws or an area of the skin showing flaws which represent a deficit in lipids due to various causes.

Example 9: Evaluation of Proliferation Rate of Preadipocytes

To confirm whether the combination of sapogenin and exosomes according to one embodiment of the present invention promotes the proliferation of 3T3-L1 preadipocytes, an experiment was performed as follows. 3T3-L1 preadipocytes were suspended in DMEM medium (Dulbecco Modified Eagle Medium) (purchased from ThermoFisher Scientific) supplemented with 10% NBCS (newborn calf serum) and 1% penicillin-streptomycin. Next, the cells were seeded into each well of a 96-well plate at a density of $8 \times 10^3$ cells/cm$^2$, and treated with pioglitazone (final concentration of 10 μM) or the combination of diosgenin (final concentration of 10 μM) and exosomes (final concentration of 6 μg/mL) prepared in Example 2. Next, the cells were cultured in an incubator at 37° C. under 5% CO$_2$ for 48 hours. After 48 hours, the cells were treated with DMEM medium containing 0.5 mg/mL of thiazolyl blue tetrazolium bromide (purchased from Sigma), and then cultured for 2 hours.

Figure 20:
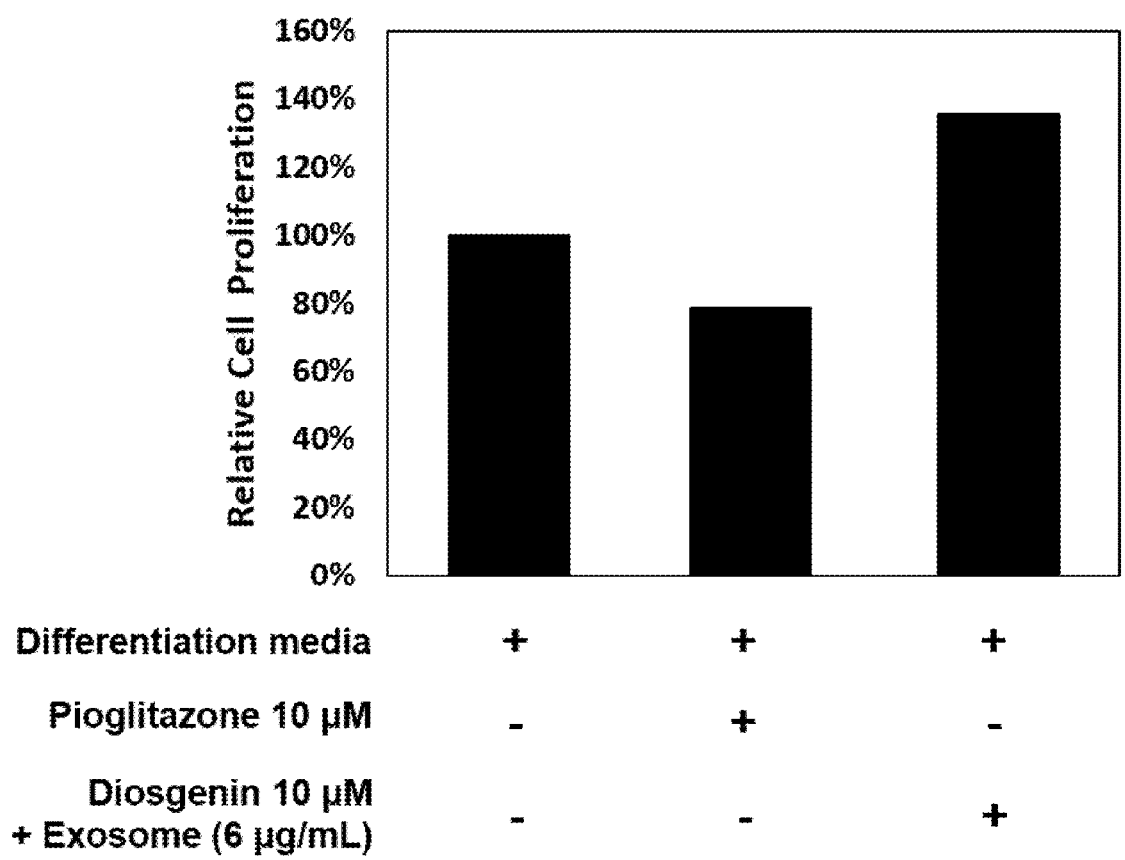
FIG. 20 is a graph showing that the proliferation rate of preadipocytes in the group treated with the combination of sapogenin and exosomes according to one embodiment of the present invention was higher than that in the group treated with pioglitazone which is a positive control.

After removing the medium, the purple crystal was dissolved with dimethyl sulfoxide (purchased from AMRESCO), and the absorbance was measured at 570 nm in order to evaluate the preadipocyte proliferation-promoting effect of the combination of sapogenin (diosgenin) and exosomes according to one embodiment of the present invention. As a result, it was confirmed that the proliferation rate of preadipocytes in the group treated with the combination of sapogenin (diosgenin) and exosomes according to one embodiment of the present invention was higher than that in the group treated with pioglitazone which is a positive control (FIG. 20).

From the aforesaid experimental results, it can be seen that the composition comprising the combination of sapogenin and exosomes according to the present invention has the effect of promoting the proliferation of preadipocytes. Therefore, when the composition of the present invention is topically applied to a part of the body showing flaws or an area of the skin showing flaws caused by a deficit in lipids, it is able to promote the proliferation of preadipocytes, and also to increase the number of the resulting adipocytes, thereby preventing, alleviating, ameliorating or recovering a part of the body showing flaws or an area of the skin showing flaws which represent a deficit in lipids due to various causes.

Although the present invention has been described with reference to the embodiments, the scope of the present invention is not limited to these embodiments. Any person skilled in the art will appreciate that various modifications and changes are possible without departing from the spirit and scope of the present invention and these modifications and changes also fall within the scope of the present invention.

We claim:

1. A method for preventing, alleviating, ameliorating or recovering a part of a body of a subject showing flaws and/or an area of a skin showing flaws caused by a deficit in lipids, the method comprising:
applying a composition comprising a combination of diosgenin and exosomes secreted from cells as an active ingredient to the part of the body and/or the area of the skin of the subject; and
promoting at least one selected from the group consisting of preadipocyte proliferation, lipid uptake into adipocytes and adipogenesis, wherein the application of the combination of diosgenin and exosomes reduces cytotoxicity caused by the diosgenin, in the part of the body and/or the area of the skin, compared to an application of the diosgenin alone, and
wherein the combination of diosgenin and exosomes is obtained by reacting the exosomes with the diosgenin at room temperature.

2. The method of claim 1, wherein the combination of diosgenin and exosomes is obtained by mixing the exosomes with the diosgenin, and incubating the mixture of the exosomes and the diosgenin at room temperature.

3. The method of claim 2, wherein the diosgenin in the combination of diosgenin and exosomes is penetrated into the exosomes or at least associated with the exosomes to be loaded in the exosomes.

4. The method of claim 1, wherein the composition is used in one or more form selected from the group consisting of a patch, a mask pack, a mask sheet, a cream, a tonic, an ointment, a suspension, an emulsion, a paste, a lotion, a gel, an oil, a pack, a spray, an aerosol, a mist, a foundation, a powder, and an oilpaper.

5. The method of claim 4, wherein the composition is applied to or soaked in at least one surface of the patch, the mask pack or the mask sheet.

6. The method of claim 1, wherein the application of the composition is performed by: (a) topically applying the composition to the part of the body and/or the area of the skin; or (b) contacting or attaching a patch, a mask pack or a mask sheet, which has the composition applied thereto or soaked therein, to the part of the body and/or the area of the skin; or (c) sequentially performing (a) and (b).

* * * * *

SEQUENCE LISTING

<160> NUMBER OF SEQ ID NOS: 16

<210> SEQ ID NO 1
<211> LENGTH: 19
<212> TYPE: DNA
<213> ORGANISM: Artificial Sequence
<220> FEATURE:
<223> OTHER INFORMATION: Pref-1 forward primer

<400> SEQUENCE: 1
tgcacactgg gttctctgg                                            19

<210> SEQ ID NO 2
<211> LENGTH: 20
<212> TYPE: DNA
<213> ORGANISM: Artificial Sequence
<220> FEATURE:
<223> OTHER INFORMATION: Pref-1 reverse primer

<400> SEQUENCE: 2
atcgtagccg caaccaacag                                           20

<210> SEQ ID NO 3
<211> LENGTH: 25
<212> TYPE: DNA
<213> ORGANISM: Artificial Sequence
<220> FEATURE:
<223> OTHER INFORMATION: PPAR-gamma forward primer

<400> SEQUENCE: 3
ggagcctaag tttgagtttg ctgtg                                     25

<210> SEQ ID NO 4
<211> LENGTH: 21
<212> TYPE: DNA
<213> ORGANISM: Artificial Sequence
<220> FEATURE:
<223> OTHER INFORMATION: PPAR-gamma reverse primer

<400> SEQUENCE: 4
tgcagcaggt tgtcttggat g                                         21

<210> SEQ ID NO 5
<211> LENGTH: 23
<212> TYPE: DNA
<213> ORGANISM: Artificial Sequence
<220> FEATURE:
<223> OTHER INFORMATION: C/EBP-alpha forward primer

<400> SEQUENCE: 5
cagcttacaa caggccaggt ttc                                       23

<210> SEQ ID NO 6
<211> LENGTH: 24
<212> TYPE: DNA
<213> ORGANISM: Artificial Sequence
<220> FEATURE:
<223> OTHER INFORMATION: C/EBP-alpha reverse primer

<400> SEQUENCE: 6
gctggcgaca tacagtacac acaa                                      24

<210> SEQ ID NO 7
<211> LENGTH: 20
<212> TYPE: DNA
<213> ORGANISM: Artificial Sequence

```
<220> FEATURE:
<223> OTHER INFORMATION: FAS forward primer

<400> SEQUENCE: 7
ttgctggcac tacagaatgc                                               20

<210> SEQ ID NO 8
<211> LENGTH: 20
<212> TYPE: DNA
<213> ORGANISM: Artificial Sequence
<220> FEATURE:
<223> OTHER INFORMATION: FAS reverse primer

<400> SEQUENCE: 8
aacagcctca gagcgacaat                                               20

<210> SEQ ID NO 9
<211> LENGTH: 19
<212> TYPE: DNA
<213> ORGANISM: Artificial Sequence
<220> FEATURE:
<223> OTHER INFORMATION: ACC forward primer

<400> SEQUENCE: 9
gcgtcgggta gatccagtt                                                19

<210> SEQ ID NO 10
<211> LENGTH: 20
<212> TYPE: DNA
<213> ORGANISM: Artificial Sequence
<220> FEATURE:
<223> OTHER INFORMATION: ACC reverse primer

<400> SEQUENCE: 10
ctcagtgggg cttagctctg                                               20

<210> SEQ ID NO 11
<211> LENGTH: 20
<212> TYPE: DNA
<213> ORGANISM: Artificial Sequence
<220> FEATURE:
<223> OTHER INFORMATION: GPDH forward primer

<400> SEQUENCE: 11
ggcaagatct gtgaccagct                                               20

<210> SEQ ID NO 12
<211> LENGTH: 20
<212> TYPE: DNA
<213> ORGANISM: Artificial Sequence
<220> FEATURE:
<223> OTHER INFORMATION: GPDH reverse primer

<400> SEQUENCE: 12
atcagcacgc tcatgggaat                                               20

<210> SEQ ID NO 13
<211> LENGTH: 22
<212> TYPE: DNA
<213> ORGANISM: Artificial Sequence
<220> FEATURE:
<223> OTHER INFORMATION: GAPDH forward primer

<400> SEQUENCE: 13
ctttggtatc gtggaaggac tc                                            22
```

```
<210> SEQ ID NO 14
<211> LENGTH: 22
<212> TYPE: DNA
<213> ORGANISM: Artificial Sequence
<220> FEATURE:
<223> OTHER INFORMATION: GAPDH reverse primer

<400> SEQUENCE: 14
gtagaggcag ggatgatgtt ct                                              22

<210> SEQ ID NO 15
<211> LENGTH: 22
<212> TYPE: DNA
<213> ORGANISM: Artificial Sequence
<220> FEATURE:
<223> OTHER INFORMATION: PPIA forward primer

<400> SEQUENCE: 15
atcttgtcca tggcaaatgc tg                                              22

<210> SEQ ID NO 16
<211> LENGTH: 20
<212> TYPE: DNA
<213> ORGANISM: Artificial Sequence
<220> FEATURE:
<223> OTHER INFORMATION: PPIA reverse primer

<400> SEQUENCE: 16
aaacgctcca tggcttccac                                                 20
```